(12) United States Patent
Thomas et al.

(10) Patent No.: US 9,200,490 B2
(45) Date of Patent: Dec. 1, 2015

(54) METHODS FOR INTERNAL CLEANING AND INSPECTION OF TUBULARS

(71) Applicant: Extreme Hydro Solutions, L.L.C., New Iberia, LA (US)

(72) Inventors: William C. Thomas, Lafayette, LA (US); William J. Thomas, III, New Iberia, LA (US); Perry J. DeCuir, Jr., Rochester Hills, MI (US)

(73) Assignee: Thomas Engineering Solutions & Consulting, LLC, New Iberia, LA (US)

( * ) Notice: Subject to any disclaimer, the term of this patent is extended or adjusted under 35 U.S.C. 154(b) by 0 days.

(21) Appl. No.: 13/832,340

(22) Filed: Mar. 15, 2013

(65) Prior Publication Data

US 2014/0090665 A1    Apr. 3, 2014

Related U.S. Application Data

(60) Provisional application No. 61/707,780, filed on Sep. 28, 2012.

(51) Int. Cl.

| | |
|---|---|
| *B08B 9/043* | (2006.01) |
| *G01N 33/00* | (2006.01) |
| *B08B 9/02* | (2006.01) |
| *B08B 9/023* | (2006.01) |
| *B08B 9/032* | (2006.01) |
| *B65G 47/14* | (2006.01) |
| *E21B 19/14* | (2006.01) |
| *B65G 47/34* | (2006.01) |
| *G01M 99/00* | (2011.01) |

(Continued)

(52) U.S. Cl.
CPC . *E21B 19/14* (2013.01); *B08B 9/02* (2013.01); *B08B 9/023* (2013.01); *B08B 9/0321* (2013.01); *B08B 9/043* (2013.01); *B65G 47/14* (2013.01); *B65G 47/34* (2013.01); *E21B 19/22* (2013.01); *E21B 37/00* (2013.01); *G01M 99/00* (2013.01); *G01N 33/00* (2013.01)

(58) Field of Classification Search
None
See application file for complete search history.

(56) References Cited

U.S. PATENT DOCUMENTS

| | | | |
|---|---|---|---|
| 1,927,847 A | 9/1933 | Resser | |
| 2,034,451 A | 3/1936 | Tripp | |

(Continued)

FOREIGN PATENT DOCUMENTS

CN    200480012199.4    3/2004

OTHER PUBLICATIONS

Technical Industries, Inc., "Vision Array" marketing brochure, publication date unknown.

(Continued)

*Primary Examiner* — Nicole Blan
*Assistant Examiner* — Pradhuman Parihar
(74) *Attorney, Agent, or Firm* — Zeman-Mullen & Ford, LLP

(57) ABSTRACT

Methods are disclosed for performing operations such as cleaning, inspection or data acquisition on an internal surface of a hollow cylindrical tubular. Preferred embodiments include providing at least one reel on which a hollow articulated lance is spooled. Tools or sensors, for example, are installed on a distal end of each lance. Hoses, electrical conduits, conductors or other similar carrier hardware inside each hollow lance supply the tools or sensors as required. A stabbing mechanism causes the reel to spool and unspool the lance so that the tools or sensors reciprocate up and down the inside of the rotating tubular.

20 Claims, 19 Drawing Sheets

(51) Int. Cl.
*E21B 37/00* (2006.01)
*E21B 19/22* (2006.01)

(56) References Cited

U.S. PATENT DOCUMENTS

| | | | |
|---|---|---|---|
| 2,114,974 A | | 4/1938 | Camerota |
| 2,500,204 A | | 3/1950 | Ronay |
| 2,519,837 A | | 8/1950 | Lampard |
| 2,585,325 A | | 2/1952 | Imshaug |
| 2,623,570 A | | 12/1952 | Resser et al. |
| 2,873,716 A | | 2/1959 | Daniel |
| 2,925,166 A | | 2/1960 | Sawdey |
| 3,492,768 A | * | 2/1970 | Schuster ............... F16F 3/00 52/108 |
| 3,571,981 A | | 3/1971 | Schaller et al. |
| 3,726,463 A | | 4/1973 | Hoffman et al. |
| 3,985,221 A | | 10/1976 | Lueders |
| 4,166,301 A | | 9/1979 | Smith |
| 4,417,363 A | | 11/1983 | Lee, Jr. |
| 4,465,422 A | | 8/1984 | Blust et al. |
| 4,508,577 A | | 4/1985 | Conn et al. |
| 4,533,055 A | | 8/1985 | Haney |
| 4,980,120 A | * | 12/1990 | Bowman ............... F28G 1/166 122/387 |
| 5,022,463 A | * | 6/1991 | Boisture ........................ 165/95 |
| 5,060,423 A | | 10/1991 | Klotz |
| 5,129,455 A | * | 7/1992 | Boisture ........................ 165/95 |
| 5,279,357 A | * | 1/1994 | Kennon et al. .................. 165/95 |
| 5,673,843 A | | 10/1997 | Gainey |
| 5,969,255 A | | 10/1999 | McLean |
| 6,290,573 B1 | | 9/2001 | Suzuki |
| 6,389,941 B1 | | 5/2002 | Michler |
| 6,615,848 B2 | | 9/2003 | Coats |
| 6,622,561 B2 | | 9/2003 | Lam et al. |
| 7,263,887 B2 | | 9/2007 | Sfeir et al. |
| 7,401,518 B2 | | 7/2008 | Sfeir et al. |
| 7,552,640 B2 | | 6/2009 | Sfeir et al. |
| 7,997,138 B2 | | 8/2011 | Sfeir et al. |
| 8,398,785 B2 | * | 3/2013 | Marschall ............... 134/168 C |
| 2002/0104471 A1 | * | 8/2002 | Awashima et al. ............ 114/382 |
| 2005/0235442 A1 | | 10/2005 | Molter |
| 2006/0249185 A1 | | 11/2006 | Garman |
| 2007/0039570 A1 | * | 2/2007 | Wilfert ........................ 122/392 |
| 2009/0196711 A1 | | 8/2009 | Gerber et al. |
| 2010/0326481 A1 | | 12/2010 | Buckner |
| 2011/0016940 A1 | * | 1/2011 | Poloni et al. .................... 72/135 |
| 2011/0017021 A1 | * | 1/2011 | Minko ........................ 75/414 |
| 2011/0030734 A1 | | 2/2011 | Marschall |
| 2011/0074332 A1 | | 3/2011 | Baker |
| 2011/0155174 A1 | * | 6/2011 | Moll et al. ........................ 134/8 |
| 2012/0074110 A1 | | 3/2012 | Zediker et al. |

OTHER PUBLICATIONS

English version of claims from Chinese Patent No. 200480012199.4.
Decuir, Perry J., "Optimizing Hydraulic Presses Using Data Acquisition Systems", proposed IFPE Paper, actual publication date unknown but prior to Feb. 1, 2012.
International Search Report and the Written Opinion of the International Searching Authority in PCT/US2014/028760 dated Aug. 26, 2014 (11 pages).

* cited by examiner

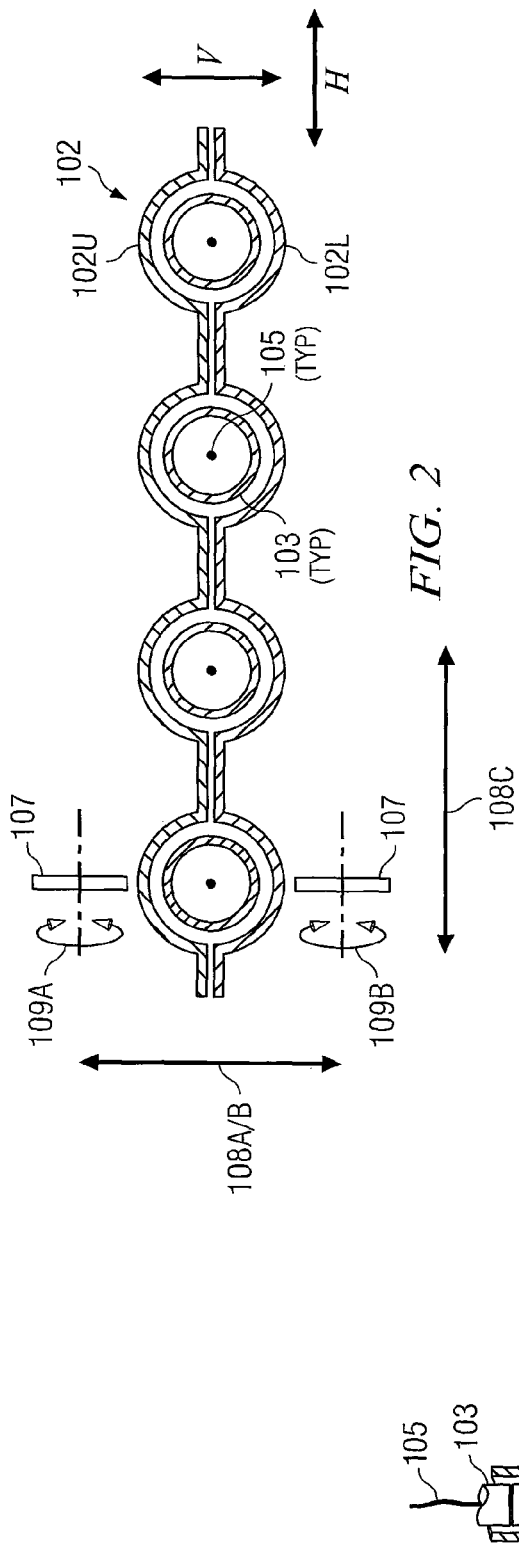
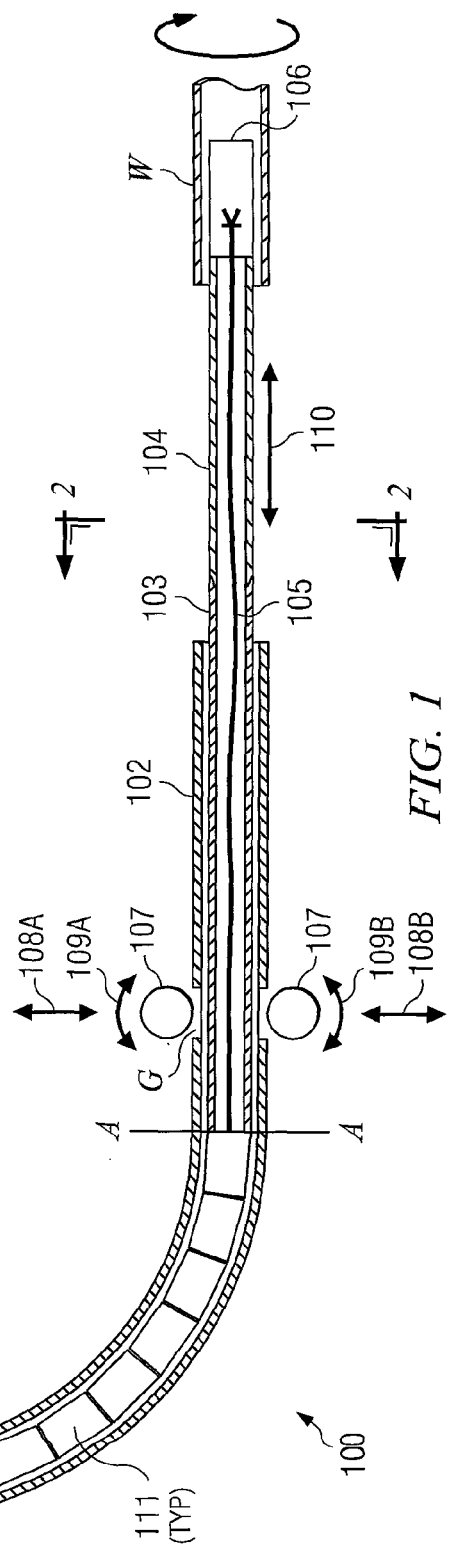
FIG. 2
FIG. 1

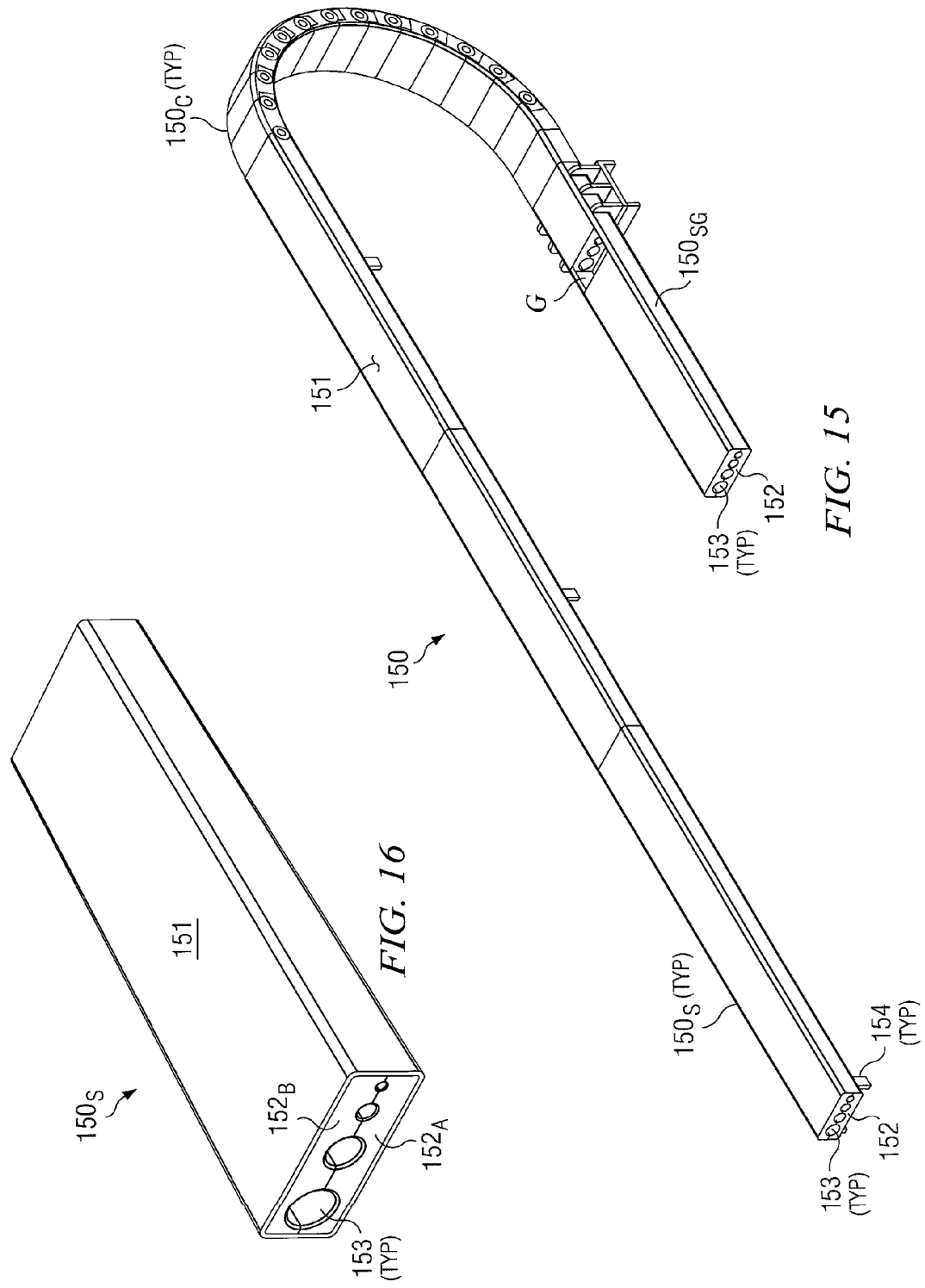

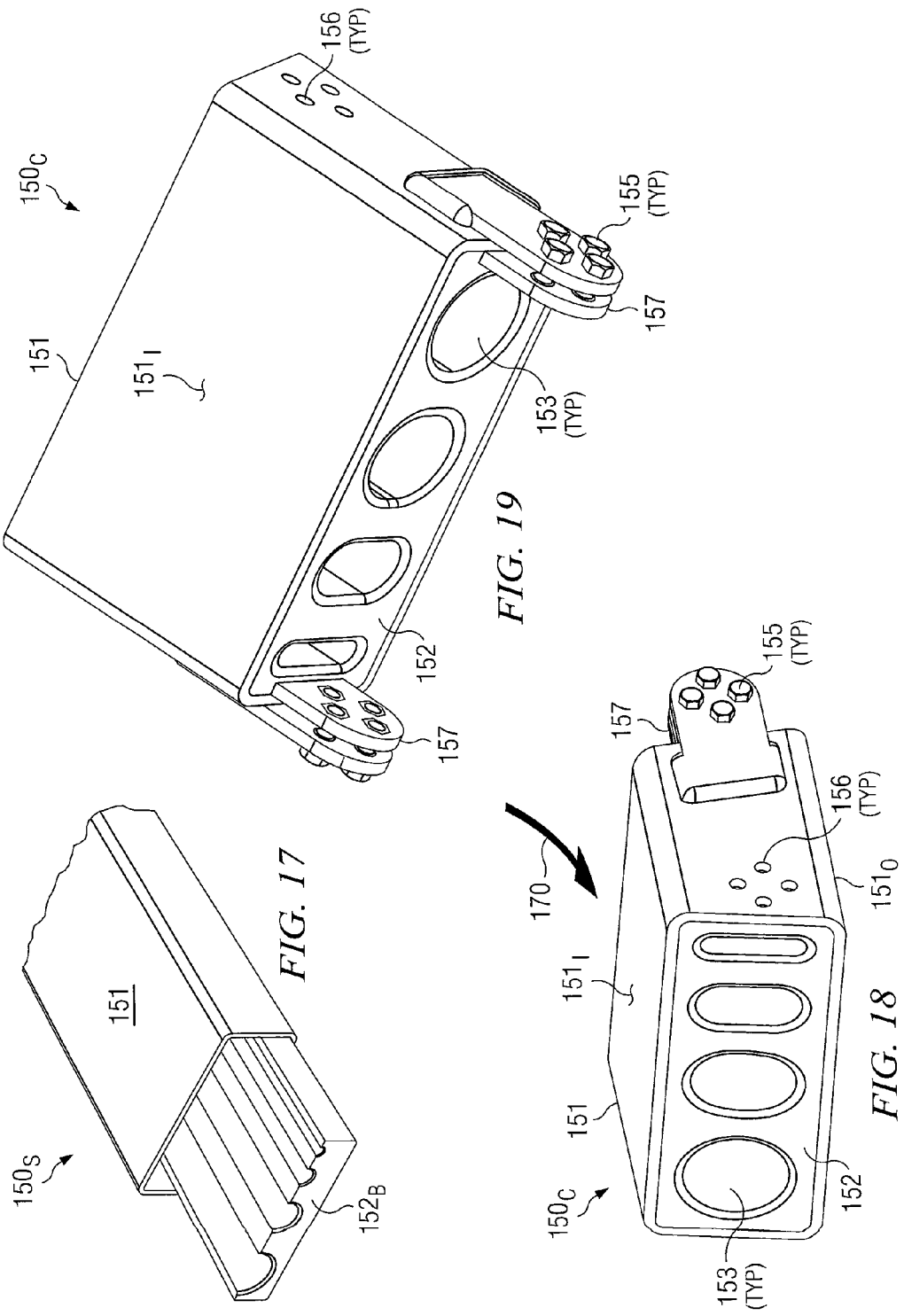

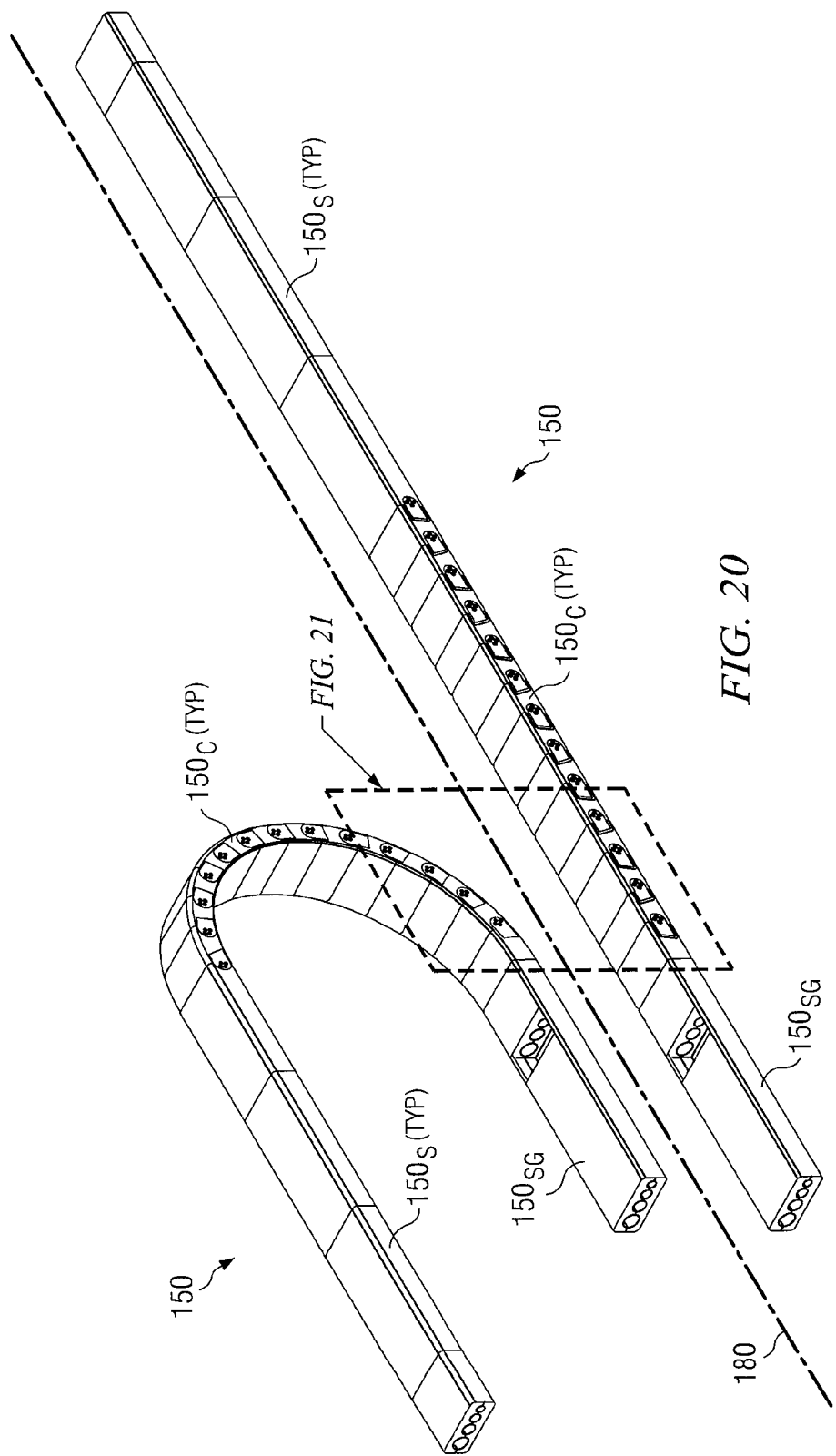

METHODS FOR INTERNAL CLEANING AND INSPECTION OF TUBULARS

RELATED APPLICATIONS

This application claims the benefit of, and priority to, commonly-assigned U.S. Provisional Application Ser. No. 61/707,780, filed Sep. 28, 2012.

FIELD OF THE INVENTION

This disclosure is directed generally to technology useful in tubular cleaning operations in the oil and gas exploration field, and more specifically to cleaning and inspecting the internals of tubulars such as drill pipe, workstring tubulars, and production tubulars.

BACKGROUND OF THE INVENTION

Throughout this disclosure, the term "Scorpion" or "Scorpion System" refers generally to the disclosed Thomas Services Scorpion brand proprietary tubular management system as a whole.

In conventional tubular cleaning operations, the cleaning apparatus is typically stationary, while the tubular is drawn longitudinally past the cleaning apparatus. The tubular is rotated at a relatively slow speed (in the range of 50 rpm, typically) while stationary, spring-loaded air motors drive spinning wire brushes and cutter heads on the inside diameter of the tubular as it is drawn past, via skewed drive rolls. These air brushes are colloquially called "cutters" although they perform abrasive cleaning operations on the internal surface of the tubular. Internal tubular cleaning operations typically also include hydroblasting in the prior art, although this is conventionally understood to be supplemental to the wire brush cleaning described above, rather than a primary cleaning process in and of itself. Typically this conventional hydroblasting is a low pressure water or steam pressure wash at pressures ranging from about 2,500 psi to 3,500 psi.

Good examples of conventional tubular cleaning apparatus are marketed by Knight Manufacturing, Inc. (formerly Hub City Iron Works, Inc.) of Lafayette, La. These products can be viewed on Knight's website.

One drawback of conventional tubular cleaning apparatus is that, with the cleaning apparatus stationary and the tubular drawn longitudinally across, the apparatus requires a large building. Range 3 drilling pipe is typically 40-47 feet long per joint, which means that in order to clean range 3 pipe, the building needs to be at least approximately 120 feet long

SUMMARY OF THE INVENTION

Aspects of the Scorpion System disclosed and claimed in this disclosure address some of the above-described drawbacks of the prior art. In preferred embodiments, the Scorpion System rotates the tubular to be cleaned (hereafter, also called the "Work" in this disclosure) while keeping the Work stationary with respect to the cleaning apparatus. The Scorpion then moves the cleaning apparatus up and down the length of the Work while the Work rotates.

In currently preferred embodiments, the Work is typically rotated at speeds in a range of about 400-500 rpm, and potentially up to 1,750 rpm under certain criteria. By contrast, the Work may also be rotated as slowly as 0.01 rpm in such currently preferred embodiments, in order to facilitate high resolution local cleaning, inspection or data gathering/analysis. However, nothing in this disclosure should be interpreted to limit the Scorpion System to any particular rotational speed of the Work. Currently preferred embodiments of the Scorpion System further draw the cleaning apparatus up and down the length of the Work at speeds within a range of about 0.5 to 5.0 linear feet per second ("fps"), depending on the selected corresponding rotational speed for the Work. Again, nothing in this disclosure should be interpreted to limit the Scorpion System to any particular speed at which the cleaning apparatus may move up or down the length of the Work.

The Scorpion System provides a multi-lance injector assembly (MLI) to clean the internal surface of the Work. The MLI provides a series of extendable and retractable lances that move up and down the internal surface of the Work as it rotates. Each lance provides tool hardware to perform a desired lance function. Examples of lance functions may include, individually or in combinations thereof, and without limitation: hydroblasting, steam cleaning, washing and rinsing, high and low volume compressed air blowing, gas drying (such as nitrogen drying), rattling head cutters, abrasive cleaning, brushing, API drift checking, sensor or other data acquisition (including visual video inspection, thermal imaging, acoustic examination, magnetic resistivity examination and electromagnetic flux examination). Data acquisition may be in the form of static or streaming data acquisition. Lances may have amplifiers on board to boost sensed or generated signals. The MLI enables extension and retraction of individual lances, one at a time, in and out of the Work. The MLI further enables a user-selected sequence of internal surface cleaning and related operations by moving different lances, according to the sequence, into and out of position for extension and retraction in and out of the Work.

Tool hardware on any particular lance may provide for single or shared operations on the lance. For example, in some exemplary embodiments, data acquisition regarding the condition of the internal surface of the Work may be via sensors provided on tool hardware shared with cleaning operations. In other embodiments, the MLI may provide a lance dedicated to data acquisition.

Similarly, in some exemplary embodiments, API drift checking may be advantageously combined with other operations on a single lance. Running an API-standard drift on a lance in and out of the Work is useful not only to check for dimensional compliance of the Work with API standards, but also to locate and hold other operational tool hardware in a desired position relative to the Work as the lance extends and retracts. Especially on larger diameter Work, it may be advantageous (although not required within the scope of this disclosure) to attach a drift-like assembly to other lance tooling in order to accomplish several advantages. A drift or drift-like assembly: (1) protects more fragile internal parts of the lance and drift mechanisms; (2) minimizes friction, especially in view of the rotational speed of the Work; and (3) keeps the lance stabilized and positioned correctly inside the Work.

In a currently preferred embodiment, the MLI provides four (4) separate lances for internal surface cleaning and related operations. Nothing in this disclosure, however, should be interpreted to limit the MLI to any particular number of lances. In the currently preferred embodiment, the four lances are provided with tooling to accomplish the following exemplary operations:

Lance 1: High pressure water blast for concrete removal and general hydroblasting operations, or steam cleaning, especially on severely rusted or scaled interior surfaces of the Work.

Lance 2: Low pressure/high temperature wash, for general tubular cleaning operations, including salt wash and rust inhibitor coating.

Lance 3: Steel Wire Brushes and/or rattling/cutter head abrasive treatment.

Lance 4: Data probes, sensors, thermal imaging devices or specialized still/video camera probes.

Referring to Lance 3 in more detail, rotating steel wire brushes and/or steel rattling heads are provided for further internal surface cleaning after high pressure and/or low pressure washing phases. In another embodiment, data sensors may be deployed instead to share Lance 2 with the above described low pressure/hot wash function. In another alternative embodiment, high or low volume compressed air or nitrogen may be deployed to Lance 3 for drying and/or expelling debris. The compressed air may also supply pneumatic tools deployed on the lance.

Yet further alternative embodiments may deploy a variety of inspection hardware on various of the lances. For example, acoustic sensors may be deployed for sonic inspection. Magnetic resistivity sensors and magnetic flux sensors (such as a hall effect sensor) may be deployed for magnetic flux inspection. Amplifiers may be deployed to boost signals.

The range of inspection options envisioned in various embodiments of the MLI is varied. For example, visual inspection via video or still cameras may identify and analyze lodged objects in the wall of the Work in real time. Geometry and circularity of the Work may be measured and tagged in real time. Visual inspection video or still cameras may also be used to examine areas of interest on the internal wall of the Work more closely. Such areas of interest may be identified and tagged by visual examination, or by other examination (earlier or at the same time) by, for example, thermal imaging, acoustic analysis or magnetic flux/resistivity analysis. Such areas of interest may include loss in tubular wall thickness, or other conditions such as pitting, cracking, porosity and other tubular wall damage.

It will be further appreciated that inspection and examination data acquired during MLI operations may also be coordinated (either in real time or later) with other data acquired regarding the Work at any other time. In particular, without limitation, inspection and examination data may be, for example, (1) coordinated with earlier data regarding the Work to provide a history on the Work, or (2) coordinated in real time with comparable data obtained concurrently regarding the exterior surface of the Work to provide a yet more detailed and high resolution analysis of the state of the Work. The scope of this disclosure is not limited in this regard.

Again, nothing in this disclosure should be interpreted to limit the MLI lances to be assigned any specific tooling to perform any specific operations. Any lance may perform any operation(s) per user selection, and may deploy any tooling suitable to perform such user-selected operation(s).

In currently preferred embodiments of the Scorpion System, the lances provided by the MLI are not self-propelling up and down within the interior of the Work. The lances are moved up and down the interior of the Work as further described in this disclosure. However, nothing in this disclosure should be interpreted to limit the lances to a non-self-propelling embodiment. Other embodiments within the scope of this disclosure may have full or partial lance propulsion functionality, including propulsion apparatus that gains traction on the interior surface of the Work.

It is therefore a technical advantage of the disclosed MLI to clean the interior of pipe efficiently and effectively. By extending and retracting interchangeable tooling on multiple lances into and out of a stationary but rotating tubular, considerable improvement is available for speed and quality of internal cleaning of the tubular over conventional methods and structure.

A further technical advantage of the disclosed MLI is to reduce the footprint required for industrial tubular cleaning. By extending and retracting lances into and out of a stationary tubular, reduced footprint size is available over conventional cleaning systems that move a tubular over stationary cleaning apparatus. Some embodiments of the MLI may be deployed on mobile cleaning systems.

A further technical advantage of the disclosed MLI is to enhance the scope, quality and reliability of inspection of the interior of the tubular before, during or after cleaning operations. Data acquisition structure may be deployed on one or more of the extendable or retractable lances. Such data acquisition structure may scan or nondestructively examine the interior of the tubular, either while the tubular is rotating or otherwise. Such data acquisition structure may include sensors, specialized visual inspection probes (such as video cameras), and/or thermal imaging probes.

The foregoing has outlined rather broadly some of the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is a functional cross-section view of aspects of one embodiment of the MLI;

FIG. 2 is a cross-section view as shown on FIG. 1;

FIGS. 14, 15, 16, 17, 18, 19, 20 and 21 illustrate aspects and features of embodiments of MLG assemblies 150;

DETAILED DESCRIPTION

Figure 3:
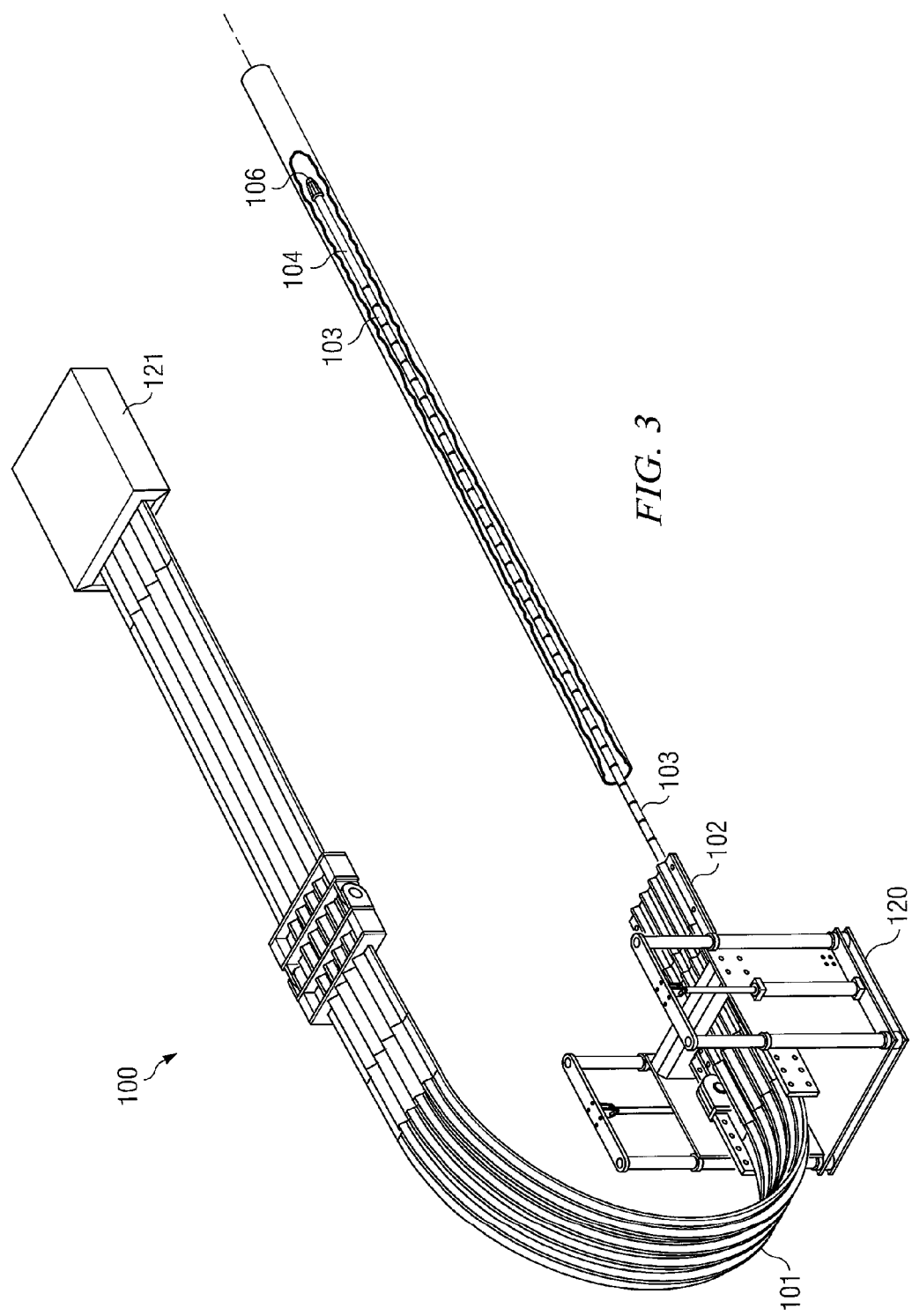
FIG. 3 is an isometric view of aspects of embodiments of the MLI.

Reference is now made to FIGS. 1 through 13 and FIGS. 8 through 11 in describing the currently preferred embodiment of the MLI.

It will be understood that the MLI, in a currently preferred embodiment, has a number of cooperating parts and mechanisms, including the Knuckle Jointed Lancer (KJL). FIGS. 1 and 2 are a functional cross-sectional representation of some of the main components included in a currently preferred embodiment of the MLI, and depict how such components cooperate in the MLI assembly. As functional representations, they will be understood not to be to scale even in a general sense. Rather, it will be appreciated that a primary purpose of FIGS. 1 and 2 is to illustrate cooperating aspects of the MLI in a conceptual sense (rather in a more structurally accurate sense), in order to facilitate better understanding of other, more structurally accurate illustrations of the MLI and KJL in this disclosure.

FIG. 1 illustrates MLI assembly 100 generally in cross-section, and depicts MLI assembly as generally comprising guide tube 101, stabbing guide tube 102, Knuckle Jointed Lancer (hereafter "KJL") 103, stinger 104, hose 105, tooling head 106 and stabbing wheels 107. In FIG. 1, MLI assembly is shown operable to clean the internal surface of tubular W. Tubular W is shown on FIG. 1 as longitudinally stationary but rotating, per earlier material in this disclosure.

With further reference to FIG. 1, KJL 103 provides stinger 104 and tooling head 106 at one end. KJL is operable to be "stabbed" into and out of rotating tubular W. It will be understood that by stabbing KJL 103 in and out of the entire internal length of rotating tubular W while tubular W rotates, MLI assembly 100 enables cleaning tools and other functional devices on tooling head 106 (such tools and devices not individually illustrated on FIG. 1) to clean, inspect, sense or otherwise perform work on the entire internal length of tubular W.

Stabbing wheels 107 on FIG. 1 enable KJL 103 to be stabbed in and out of tubular W. It will be appreciated from FIG. 1 that guide tube 101 and stabbing guide 102 generally encase KJL 103 up until the general area where stinger 104 and tooling head 106 lead the "stabbing" (that is, the extension and retraction) of KJL 103 into and out of tubular W. Stabbing guide 102 provides gaps G where the outside surface of KJL 103 is exposed. In a currently preferred embodiment, gaps G are rectangular openings in stabbing guide 102, although this disclosure is not limited in this regard. Directional arrows 108A and 108B on FIG. 1 represent where stabbing wheels 107 are operable to be moved together and apart so that, via gaps G, the circumferences (or "treads") of stabbing wheels 107 can engage and disengage the outer surface of KJL 103 on opposing sides. Thus, when stabbing wheels 107 are engaged on the outer surface of KJL 103 and rotated, per directional arrows 109A and 109B on FIG. 1, they become operable to move KJL 103 per directional arrow 110.

With further reference to FIG. 1, KJL 103 and stinger 104 encase 105. Hose 105 on FIG. 1 is a functional representation of any type of flexible supply that tooling on tooling head 106 may require, such as, purely for example, steam hoses, water hoses, air hoses, nitrogen gas hoses, or conduits comprising electrical power supply cords, data transfer wiring, solid conductors, coils or antennae. Nothing in this disclosure shall be interpreted to limit hose 105 to any particular type of flexible supply or combination thereof.

Discussing hose 105 in more detail, in currently preferred embodiments, the hoses are designed and manufactured for extended life in high temperature and high pressure service, and further comprise a customized armor system for protection on the outside, including an outer co-flex, stainless steel wall with flexible steel armoring and rigidity packing. The rigidity packing uses heat-shrinking material to form a solid ID-OD fusion bond in the hoses, while also filling the void between the outer armor system and the specially-designed high temperature and high pressure hoses. It will be appreciated, however, that these hose specifications are exemplary only, and that nothing in this disclosure should be interpreted to limit hose 105 on FIG. 1 to a particular specification.

It will be further understood that in embodiments where hoses 105 are specified per the example above for extended hose service life, the cost per unit length of the high-specification hose is significantly higher than the corresponding cost of conventional hose. In order to optimize this increased cost, hose 105 on FIG. 1 may, in some alternative embodiments, provide a connector separating a portion of conventional hose from a portion of higher specification hose. Advantageously, the portion of high-specification hose is positioned within KJL 103 and stinger 104 at the distal end thereof, connected to tooling head 106, and is long enough so that when KJL 103 is extended all the way to the very far (distal) end of tubular W, the entire length of tubular W is served by high-specification hose. The remaining portion of hose 105 will then be understood to be resident in the portion of KJL 103 that remains in guide tube 101 even when KJL 103 is extended all the way to the very far end of tubular W. This remaining portion of hose 105 may be deployed as conventional hose since it is not subject to the rigors of service within tubular W.

Although FIG. 1 illustrates a single hose 105 deployed in KJL 103, it will be appreciated that this disclosure is not limited to any particular number of hoses 105 that may be deployed in a single KJL 103. Multiple hoses 105 may be deployed in a single KJL 103, according to user selection and within the capacity of a particular size of KJL 103 to carry such multiple hoses 105. This "multiple hose 105 per KJL 103" aspect of MLI 100 is described in greater detail further on in this disclosure, with reference to FIG. 14.

With reference now to graphical separator A-A on FIG. 1, it will be appreciated that the portion of KJL 103 to the right of A-A on FIG. 1 is in cross-section, while the portion to the left is not. FIG. 1, to the left of graphical separator A-A, thus illustrates that a portion of the length of KJL 103 comprises a concatenated and articulated series of hollow, generally trapezoidal KJL segments 111. KJL segments 111 (and their generally trapezoidal profile) will be described in detail further on in this disclosure. However, it will be seen from FIG. 1 that the concatenated, articulated nature and general trapezoidal profile of KJL segments 111 allow KJL 103, when the distal end thereof is being stabbed in and out of tubular W, to correspondingly slide around curved portions of guide tube 101 with reduced bending stress.

FIG. 2 is a cross-sectional view as shown on FIG. 1. Items depicted in both FIGS. 1 and 2 have the same numeral.

It will be immediately seen on FIG. 2 that, consistent with earlier material in this disclosure, a preferred embodiment of MLI assembly 100 provides 4 (four) separate and independent lances for cleaning, inspection, data acquisition and related operations (although as noted above, nothing in this disclosure should be construed to limit MLI assembly 100 to four lances). On FIG. 2, stabbing guide 102 includes upper and lower stabbing guide pieces 102U and 102L, which may be held together by conventional fasteners such as bolts and nuts. Stabbing guide 102 further encases 4 (four) separate KJL 103 assemblies. Each KJL 103 encases a hose 105. It will be understood that KJL 103, stinger 104 (not illustrated on FIG. 2), hose 105 and tooling head 106 (also not illustrated on FIG. 2) are functionally the same for each of the 4 (four) lance deployments illustrated on FIG. 2. It will be further appreciated that the disclosure above associated with FIG. 1 directed to extension and retraction of a single KJL 103 applies in analogous fashion to additional KJL assemblies 103 deployed on a particular embodiment of MLI assembly 100.

As also mentioned above with reference to FIG. 1, it will be appreciated that although FIG. 2 illustrates a single hose 105 deployed in each KJL 103, it will be appreciated that this disclosure is not limited to any particular number of hoses 105 that may be deployed in any single KJL 103. Multiple hoses 105 may be deployed in any single KJL 103, according to user selection and within the capacity of a particular size of KJL 103 to carry such multiple hoses 105. This multi-hose 105 and multi-size KJL 103 aspect of MLI 100 is described in greater detail further on in this disclosure, with reference to FIG. 14.

Although not illustrated on FIGS. 1 and 2, currently preferred embodiments of guide tubes 101 and stabbing guide 102 provide a low-friction coating on the internal surface thereof. This low-friction coating assists a sliding movement of KJL 103 through guide tubes 101 and stabbing guide 102 as KJL 103 is extended and retracted into and out of tubular W.

FIG. 2 also shows stabbing wheels 107. Consistent with FIG. 1, directional arrow 108A/B on FIG. 1 represents where stabbing wheels 107 are operable to be moved together and apart so that, via gap G (not shown on FIG. 2), the circumferences (or "treads") of stabbing wheels 107 can engage and disengage the outer surface of KJL 103 on opposing sides. Directional arrows 109A and 109B on FIG. 2 represent, consistent with FIG. 1, that rotation of stabbing wheels 107 when engaged on the outer surface of KJL 103 will cause KJL 103 to extend and retract.

Directional arrow 108C on FIG. 2 represents that when stabbing wheels 107 are disengaged, stabbing guide 102 (or, in other embodiments, stabbing wheels 107) is/are further operable to be moved laterally to bring any available KJL 103, according to user selection, between stabbing wheels 107. In this way, any available KJL 103, according to user selection, may be called up for engagement by stabbing wheels 107 and subsequent extension into and retraction out of tubular W.

Directional arrows H and V on FIG. 2 represent generally that the entire MLI assembly 100 as described on FIGS. 1 and 2 may be adjusted horizontally and vertically to suit size (diameter), wall thickness and relative position of tubular W into which KJL 103 assemblies are to be inserted. Such adjustment allows MLI assembly 100 to work on a wide range of different sizes and thicknesses of tubulars W.

With reference now to FIG. 3, a more scale-accurate representation of MLI assembly 100 is illustrated. Items depicted on FIG. 3 that are also depicted on FIGS. 1 and 1B have the same numeral. FIG. 3 depicts tubular W with a partial cutout, allowing KJL 103 (with stinger 104 and tooling head 106 on the distal end of KJL 103) to be seen extending into nearly the entire length of rotating tubular W. FIG. 3 further depicts guide tube 101 and stabbing guide 102.

Adjustment assembly 120 on FIG. 3 enables the positional adjustments described above with reference to FIGS. 1 and 2. More specifically, adjustment assembly 120 includes structure that enables (1) stabbing wheels 107 to move together and apart per directional arrows 108A and 108B on FIGS. 1 and 2, (2) stabbing guide 102 to move laterally per directional arrow 108C on FIG. 2, and (3) MLI assembly 100 to move horizontally and vertically per directional arrows H and V on FIG. 2.

Although adjustment assembly 120 (and components thereof) are illustrated and describe generally in this disclosure, it will be appreciated that the specifics of adjustment assembly 120, and the control thereof, rely on conventional hydraulic, pneumatic or electrical apparatus, much of which has been omitted from this disclosure for clarity.

FIG. 3 further illustrates hose box 121. It will be appreciated that as KJL assemblies 103 are fully extended all the way to the distal end of tubular W, and then retracted all the way out of tubular W, corresponding hoses 105 deployed inside KJL assemblies 103 require surplus length to accommodate such extension and retraction. Hose box 121 is a containment box for such surplus lengths of hoses 105.

Figure 4:
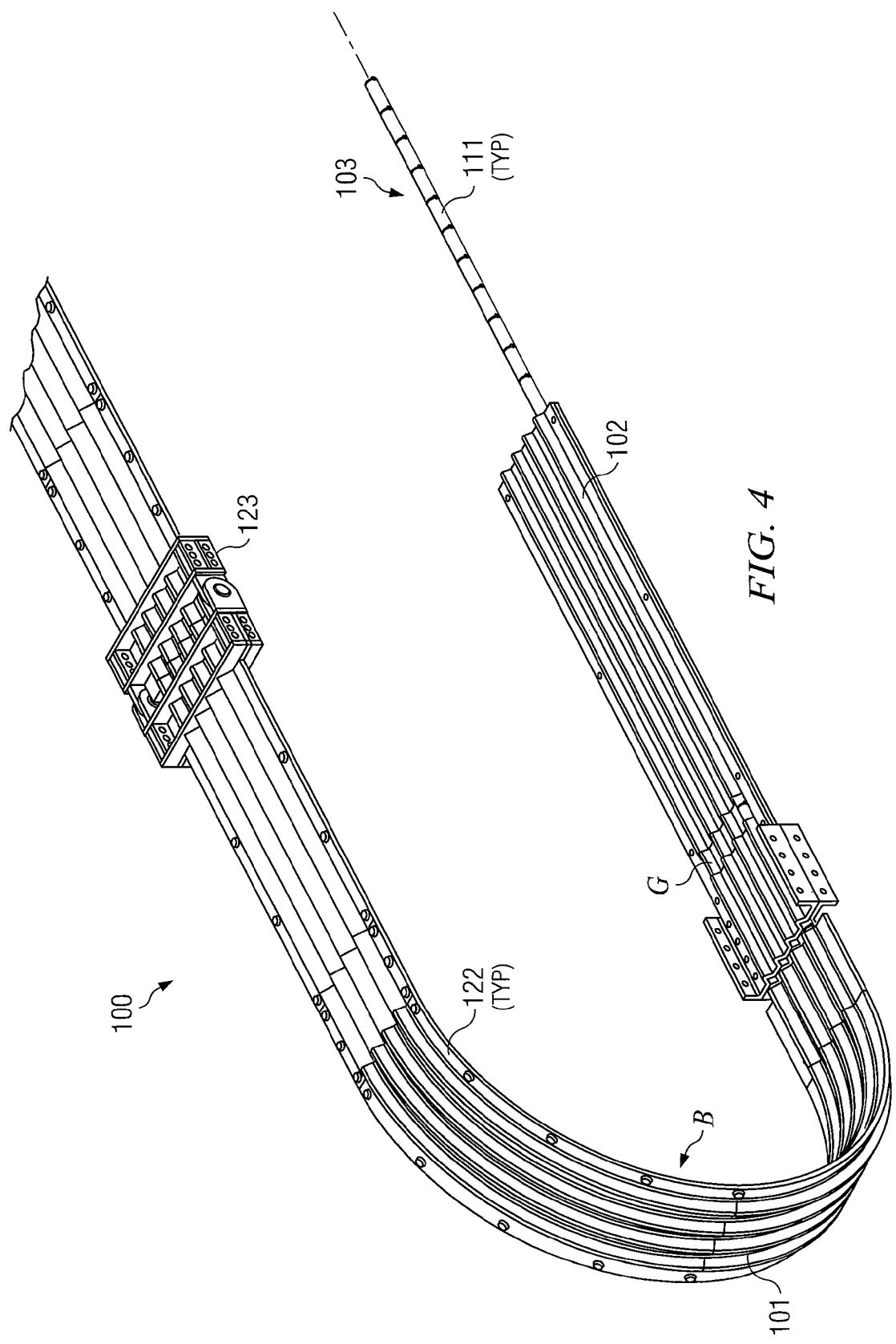
FIG. 4 is a general enlargement of MLI assembly 100 as illustrated on FIG. 3.

FIG. 4 is a general enlargement of MLI assembly 100 as illustrated on FIG. 3, particularly in the area around stabbing guide 102. Adjustment assembly 120 and tubular W on FIG. 3 have been omitted on FIG. 4 for clarity. As in other illustrations in this disclosure depicting aspects of MLI assembly 100, items depicted on FIG. 4 that are also depicted on FIGS. 1, 2 and/or 3 have the same numeral.

FIG. 4 illustrates stabbing guide 102 with one exemplary KJL 103 extended. Gaps G from FIG. 1 can also be seen on stabbing guide 102 on FIG. 4. It will be recalled from earlier disclosure describing FIG. 1 that the "treads" of stabbing wheels 107 (not shown on FIG. 4) contact the outer surface of KJL assemblies 103 through gaps G to enable, via rotation of stabbing wheels 107, extension and/or retraction of KJL assemblies 103.

FIG. 4 further illustrates guide tubes 101 as assemblies operable to be disassembled and reassembled. This aspect of guide tubes 101 enables, in part, MLI assembly 100 to be configured in either "curved tube" mode (as illustrated on FIG. 4) or "straight tube" mode (not illustrated) as further described below. It will be seen on FIG. 4 that in currently preferred embodiments, guide tubes 101 are separable along their travelling horizontal axis (or thereabouts) and are further operably held together during service with guide tube fasteners 122. Longitudinal sections of guide tubes 103 are further separable at guide tubes joints 123 (only one exemplary guide tube joint 123 fully illustrated on FIG. 4).

It will be seen from FIG. 4 that optimization of footprint of MLI assembly 100 may be assisted by deploying guide tubes 101 as illustrated in FIG. 4, with guide tubes 101 undergoing a u-turn of approximately 180 degrees at bend B during their travel. Although also not illustrated in FIG. 4, nothing in this disclosure should be construed to limit bend B to a u-turn of 180 degrees or thereabouts. Other angles of bend B are considered within the scope of this disclosure.

Other embodiments of the MLI assembly 100 (such other embodiments not illustrated) provide guide tubes 101 substantially straight, extending substantially horizontally up to the entrance to tubular W, and substantially parallel to the longitudinal axis of tubular W. It will be appreciated that such "straight tube" embodiments will require additional footprint. Some of such "straight tube" embodiments may also substitute rigid pipes for KJL assemblies 103. With momentary reference to FIG. 1, rigid pipes in "straight tube" embodiments (not illustrated) will surround hoses 105 instead of KJL assemblies 103 and stingers 104, and will further connect directly to tooling heads 106. It will be appreciated that extension and retraction of the rigid pipes may then be enabled via stabbing wheels 107 operating on the exterior surfaces of rigid pipes through gaps G in stabbing guide 102, per FIG. 1).

Figure 5:
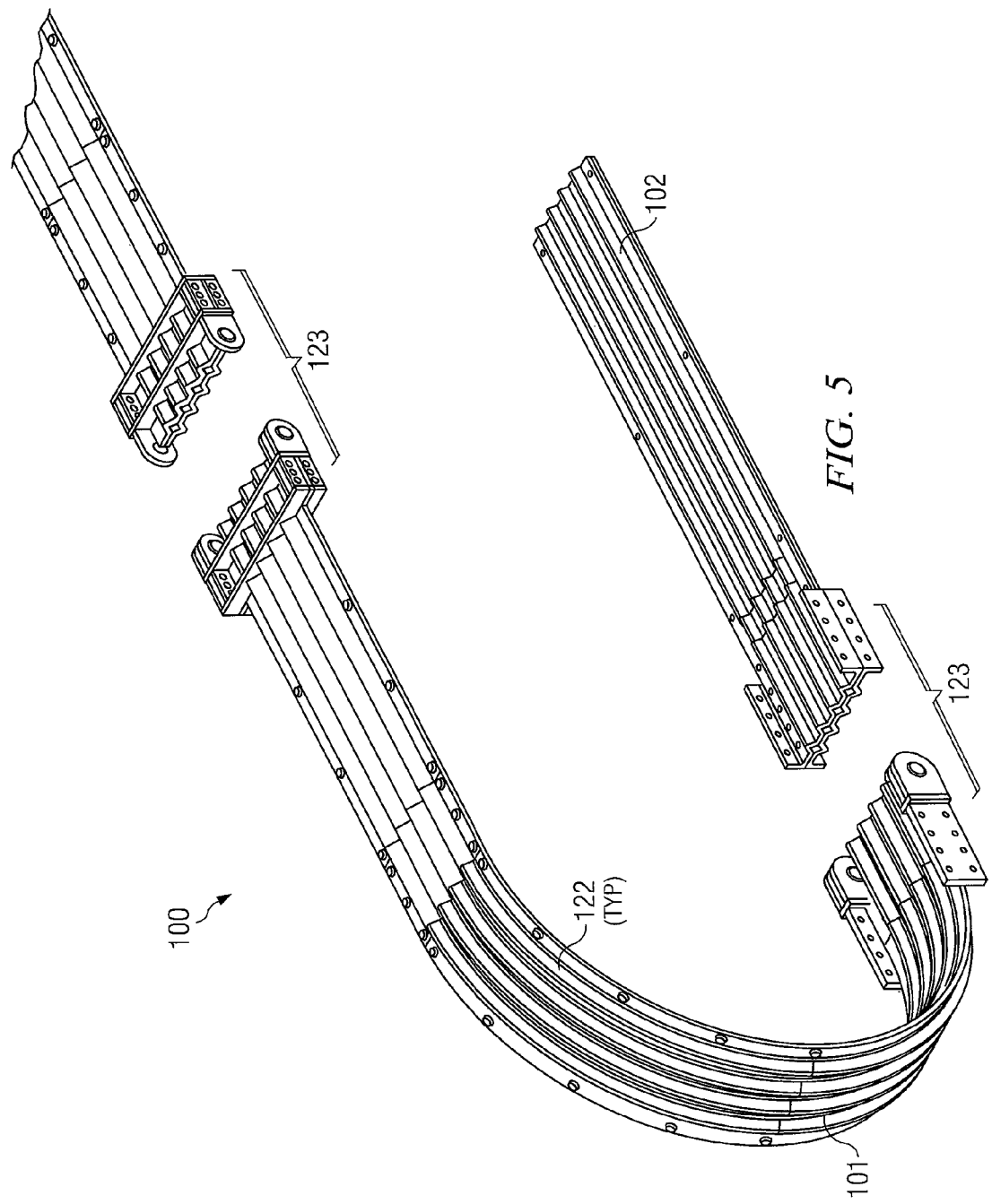
FIGS. 5 and 6 are exploded views of aspects also illustrated on FIG. 4.
Figure 6:
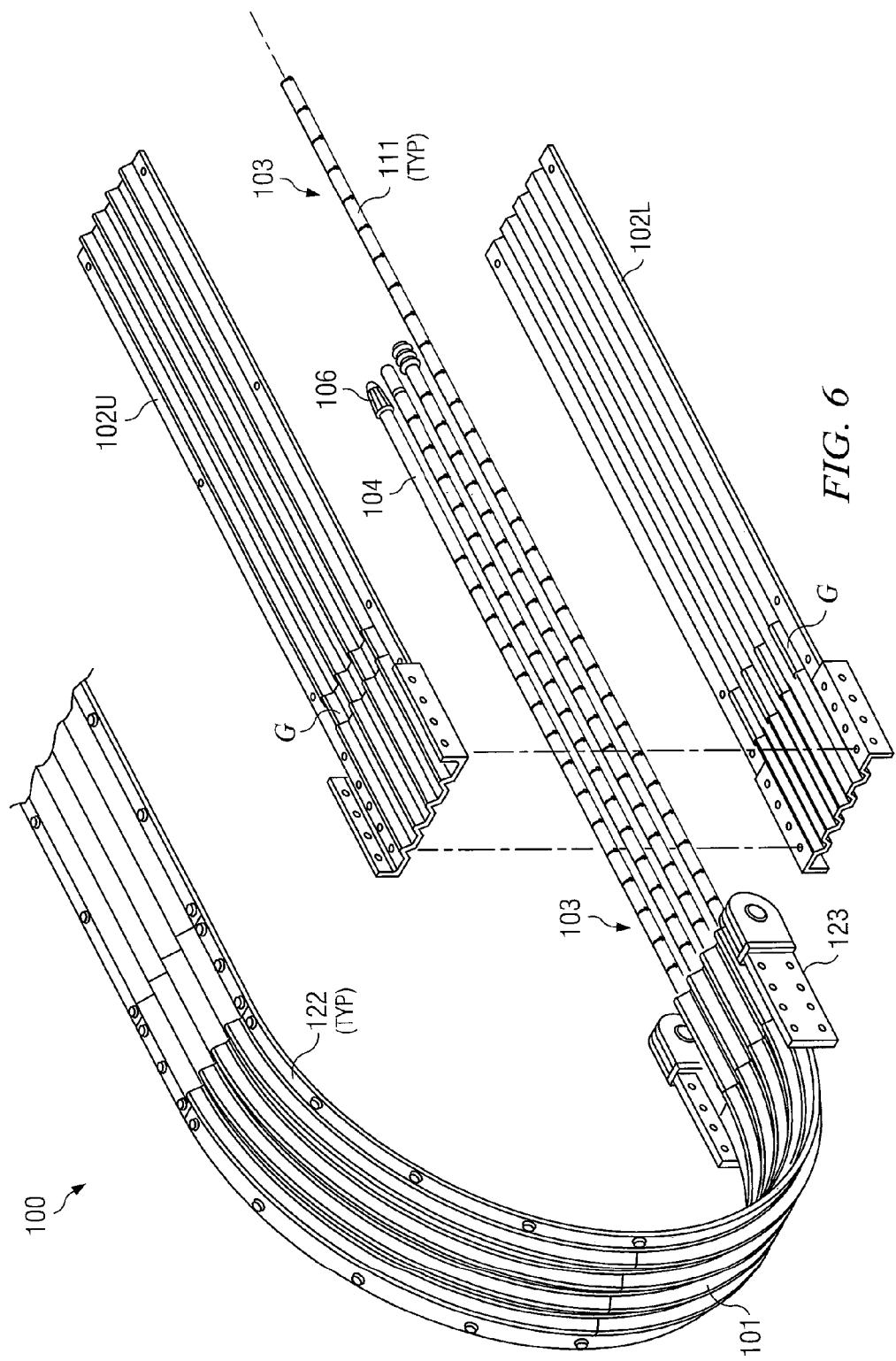

With reference now to FIGS. 5 and 6, guide tubes 101 and stabbing guide 102 are shown in partially "exploded" form in order to illustrate how certain embodiments of MLI assembly 100, now to be illustrated and described in more detail, may be "converted" back and forth, per user selection, between a "curved tube" mode (as illustrated in FIG. 4), and a "straight tube" mode as described above although not illustrated. As before, items depicted on FIGS. 5 and 6 that are also depicted on FIGS. 1 through 4 have the same numeral.

It will be recalled from earlier disclosure referring to FIG. 4 that "convertible" embodiments of MLI assembly 100 provide guide tubes 101 operable to be disassembled and reassembled in order to convert between "curved tube" and "straight tube" modes. FIG. 5 illustrates MLI assembly 100 in "curved tube" mode, with guide tube 101 and stabbing guide 102 disassembled at guide tube joints 123. It will be seen in the exemplary embodiment illustrated on FIG. 5 that two guide tube joints 123 are provided, one at the connection between guide tubes 101 and stabbing guide 102, and the other at a connection between pieces of guide tubes 101 above stabbing guide 102. It will be nonetheless understood that the number and location of guide tube joints 123 illustrated on FIG. 5 are exemplary only. Nothing in this disclosure should be interpreted to limit MLI assembly 101 to any particular number or location of guide tube joints 123.

FIG. 6 illustrates MLI assembly 100 in "curved tube" mode with upper and lower stabbing guide pieces 102U and 102L separated. As noted above with reference to FIG. 4, fasteners 122 may hold sections of guide tube 101 and stabbing guide 102 together at the traveling horizontal axis thereof. In such an embodiment, fasteners 122 may be unfastened in order enable disassembly. It will be appreciated with referenced to FIG. 6 that although not illustrated, sections of guide tubes 101 may also be separated at their traveling horizontal axis by unfastening fasteners 122 in analogous fashion to the manner in which FIG. 6 illustrates stabbing guide pieces 102U and 102L as separated.

By way of reference, with FIG. 6 illustrating stabbing guide pieces 102U and 102L as separated, FIG. 6 further illustrates KJL assemblies 103, stingers 104, tooling heads 106, KJL segments 111 and gaps G in more scale-accurate fashion than on FIGS. 1 and 1B, where they were illustrated in more of a functional form.

Visualizing FIGS. 5 and 6 together, therefore, it will be appreciated that by disassembling and separating guide tubes 101 at their traveling horizontal axes per FIG. 6, and by separating pieces thereof at guide tube joints 123 per FIG. 5, guide tubes 101 may be disassembled and removed from MLI assembly 100.

Figure 7:
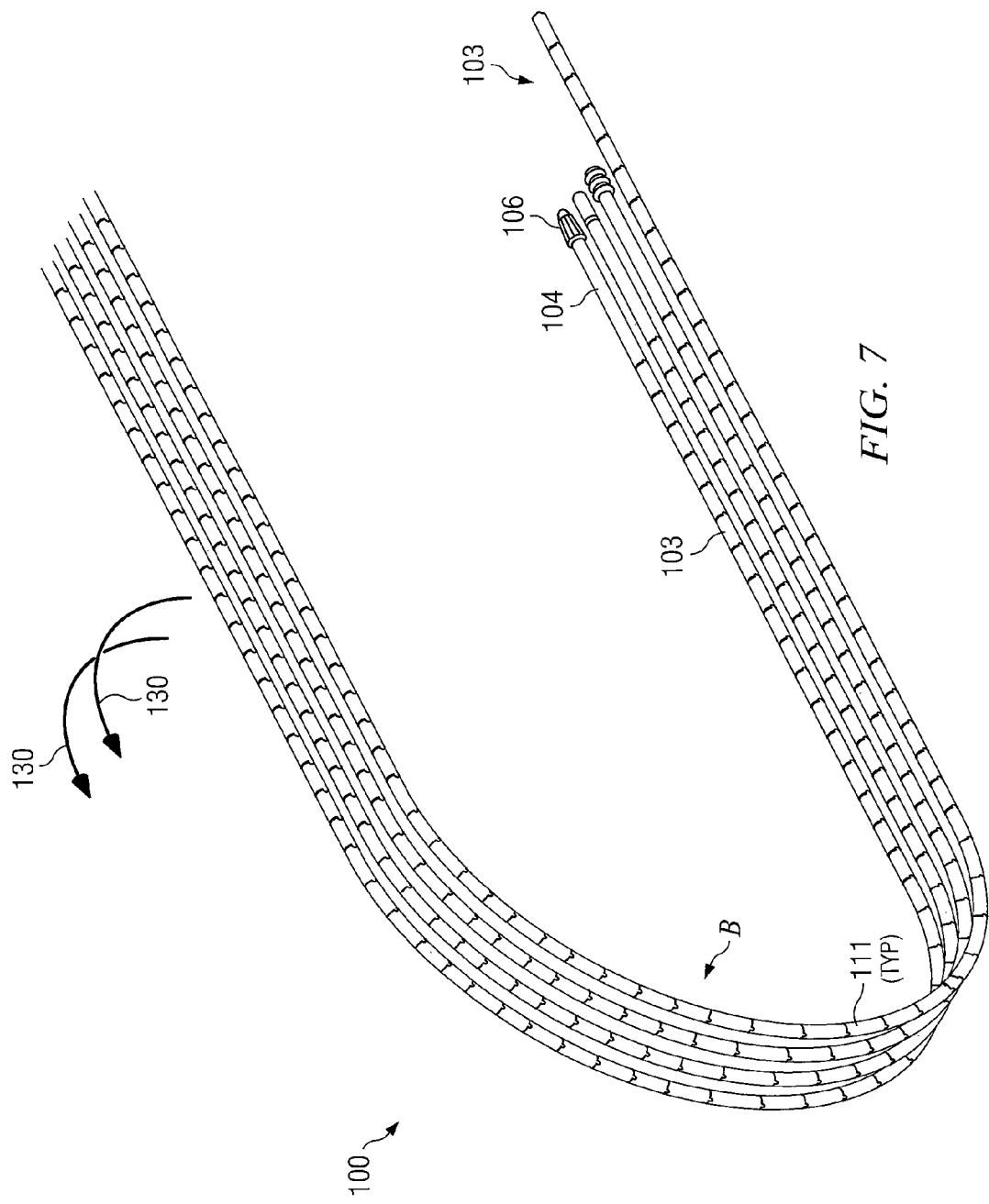
FIG. 7 is an isometric view of aspects of embodiments of KJL assemblies 103 in isolation.

Disassembly and removal of guide tubes 101 in turn exposes KJL assemblies 103 along their entire length, as illustrated on FIG. 7. As before, items depicted on FIG. 7 that are also depicted on FIGS. 1 through 6 have the same numeral. FIG. 7 further illustrates KJL assemblies 103 comprising KJL segments 111. In more detail, it will be recalled from earlier disclosure with reference to FIG. 1 that KJL assemblies 103 each comprise a concatenated and articulated series of hollow, generally trapezoidal KJL segments 111.

Referring back now to the general "conversion" procedure between "curved tube" and "straight tube" modes, it will be appreciated that FIG. 7 illustrates KJL assemblies 103 in "curved tube" mode. It will be further visualized from FIG. 7 that by following directional arrows 130, the articulated, generally trapezoidal nature of concatenated KJL segments 111 enables KJL assemblies 103 to be laid out horizontally straight from their previous "curved tube" configuration (per FIG. 7) once guide tubes 101 are disassembled and removed. It will be then understood that KJL assemblies 103 will be in "straight tube" configuration once laid out straight and horizontal. Rigid pipes (per earlier disclosure) or straight guide tubes in pieces (not illustrated) may then be installed around straight and horizontal KJL assemblies 103. MLI assembly 100 will then be in "straight tube" mode.

It will be appreciated that conversion back to "curved tube" mode requires generally the reverse process. KJL assemblies 103, in straight and horizontal configuration are exposed by removal of their surrounding rigid pipes or straight guide tubes. The articulated, generally trapezoidal nature of concatenated KJL segments 111 enables KJL assemblies 103 to be "rolled over" in the opposite direction of directional arrows 130 on FIG. 7. When "rolled over" to the user-desired bend B (per FIG. 7), KJL assemblies 103 will be in "curved tube" configuration. Guide tubes 101 may be reassembled around KJL assemblies 103 per the reverse of the disassembly process described above with reference to FIGS. 5 and 6. MLI assembly 101 will then be "curved tube" mode again.

Figure 8:
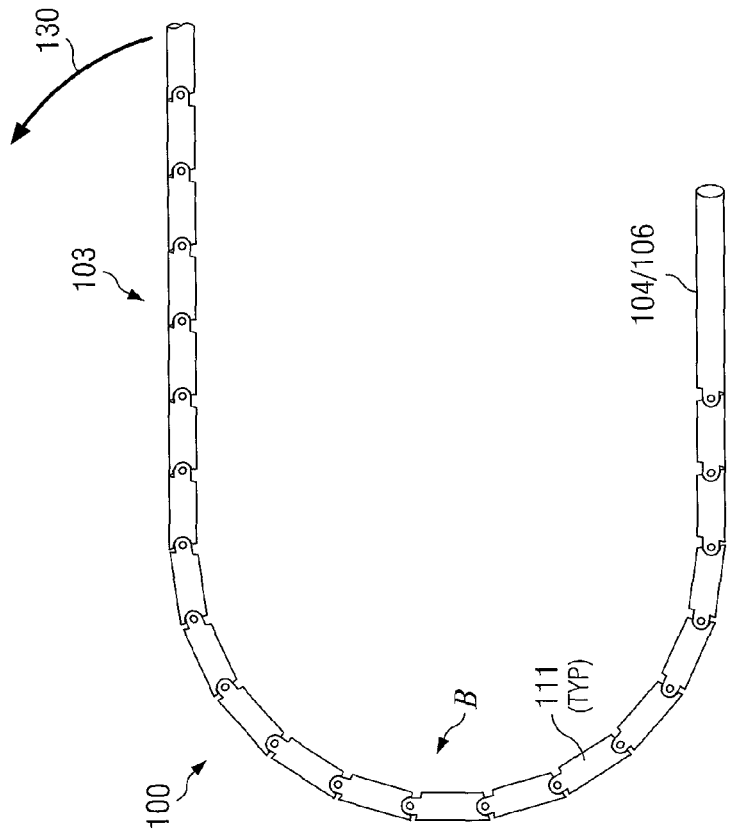
FIGS. 8, 9, 10 and 11 illustrate aspects and features of embodiments of KJL assemblies 103.
Figure 9:

FIGS. 8 and 9 illustrate, in conceptual and functional form, the preceding two paragraphs' disclosure of the currently preferred embodiment of "conversion" back and forth, per user selection, of "curved tube" and "straight tube" modes. As before, items on FIGS. 8 and 9 also shown on FIGS. 1 through 7 have the same numeral. On FIG. 8, with further reference to FIG. 7, MLI assembly 100 is in "curved tube" mode with KJL 103 curved around bend B. Stinger 104 and tooling head 106 are shown conceptually on FIGS. 8 and 9 for reference. FIGS. 8 and 9 further show, again conceptually and functionally rather than to scale, that KJL 103 comprises a concatenated string of articulated, generally trapezoidal KJL segments 111.

By following directional arrow 130 on FIG. 8, KJL 103 may be laid out flat and horizontal as shown on FIG. 9. The concatenated string of articulated, generally trapezoidal KJL segments 111 enables KJL to be laid out flat and horizontal, in configuration for "straight tube" mode.

FIG. 9 further shows that by following directional arrow 130R (the reverse of directional arrow 130 on FIG. 8), KJL 103 may be "rolled up" again to form bend B, as shown on FIG. 8. The concatenated string of articulated, generally trapezoidal KJL segments 111 enables KJL 103 to be rolled up, in configuration for "curved tube" mode.

Figure 10:
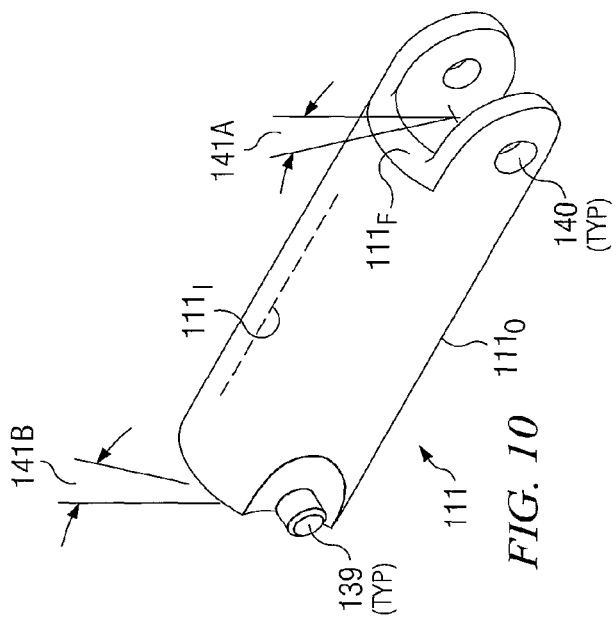

The articulated, generally trapezoidal nature of KJL segments 111 will now be discussed in greater detail. FIG. 10 illustrates a currently preferred design of an individual KJL segment 111. As before, items on FIG. 10 also shown on FIGS. 1 through 9 have the same numeral.

It will be understood that FIG. 10 illustrates just one example of a design of a KJL segment 111. Many types of individual design of KJL segments 111 are available within the scope of this disclosure, and the design of KJL segment 111 on FIG. 10 is exemplary only. Likewise, the size (diameter), number and length of individual KJL segments 111 in a particular KJL 103 may be per user design according to curvature and other geometric parameters of a particular MLI deployment. Nothing in this disclosure should be interpreted to limit the MLI to any particular length, size (diameter), number or even uniformity of KJL segments 111 that may be included in KJL 103.

Referring now to FIG. 10, KJL segment 111 provides pins 139 at one end (one pin hidden from view) and lug holes 140 at the other end. By linking the pins 139 of one KJL segment 111 into the lug holes 140 of the next in line, a plurality of KJL segments 111 may be concatenated into an articulated string, as illustrated in FIGS. 8 and 9, and elsewhere in this disclosure.

KJL segment 111 on FIG. 10 also has opposing longitudinal outer surfaces $111_I$ and $111_O$ which, when a plurality of KJL segments 111 are articulated together into a string thereof, will form the inner and outer surfaces of curvature respectively of the rolled-up articulated string. KJL segment 111 on FIG. 10 further provides opposing faces $111_F$. Opposing faces $111_F$ are configured to slope towards one another. This sloping is illustrated on FIG. 10 at items 141A and 141B, where the planes of faces $111_F$ are illustrated to have angular deviation from a theoretical face plane that would be normal to the longitudinal axis of the KJL segment 111. In this way, the length of KJL segment 111 is less along longitudinal surface $111_I$ than it is along longitudinal surface $111_O$. Accordingly, when a plurality of KJL segments 111 are articulated into a string such that longitudinal surfaces $111_I$ and $111_O$ line up along the string, the shorter lengths of surfaces $111_I$ permit "rolling up" where surfaces $111_I$ form the innermost surface of curvature, and surfaces $111_O$ form the outermost surfaces of curvature.

Figure 11:
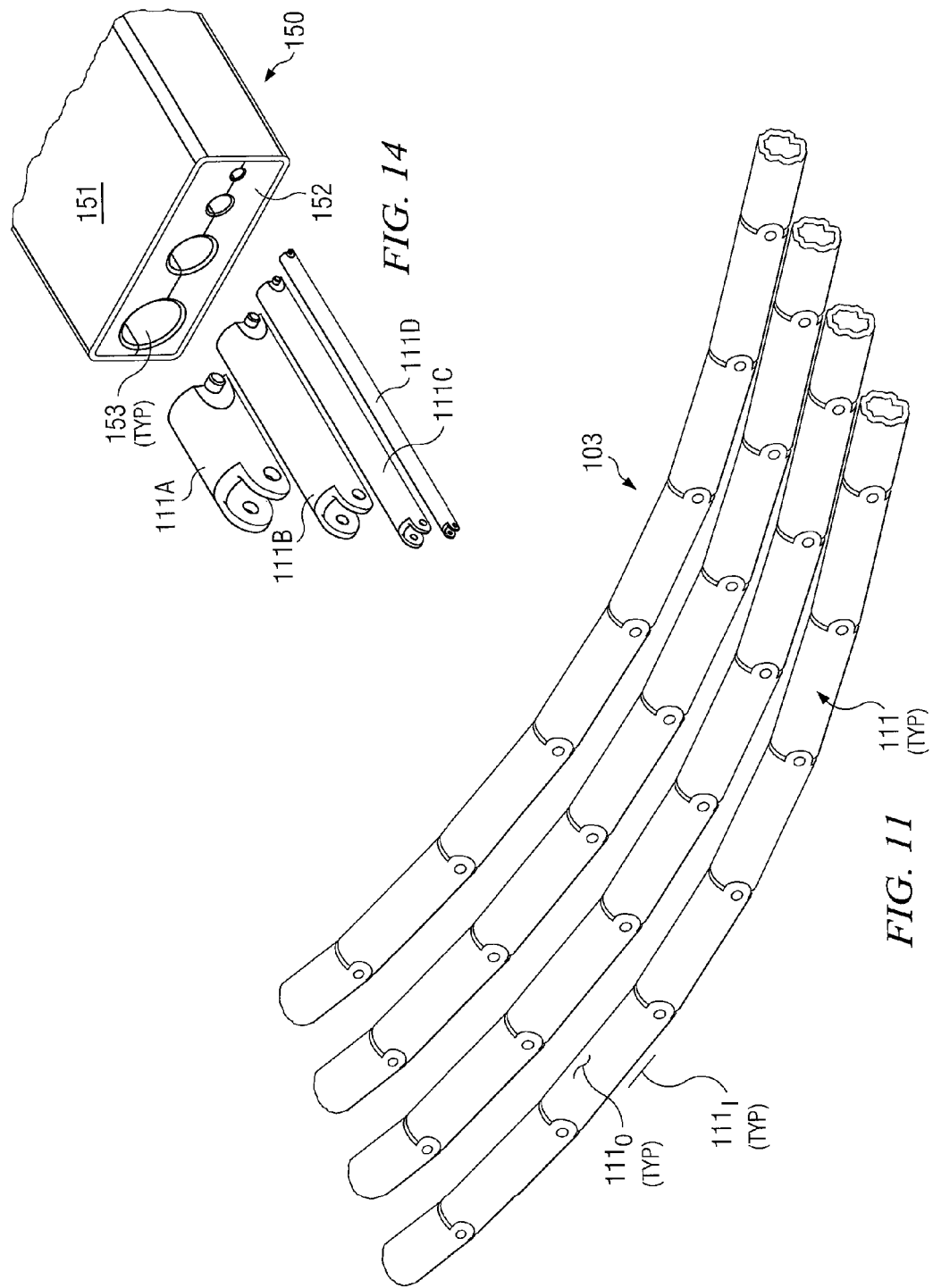

FIG. 11 illustrates KJL 103 comprising a concatenation of articulated KJL segments 111 designed per the example of FIG. 10. As before, items on FIG. 11 that are also shown on FIGS. 1 through 10 have the same numeral.

As described above with reference to FIG. 10, FIG. 11 shows that by linking the pins 139 of one KJL segment 111 into the lug holes 140 of the next in line, a plurality of KJL segments 111 may be concatenated into an articulated string. Further, the shorter lengths of longitudinal surfaces $111_I$ over longitudinal surfaces $111_O$ enable curvature when KJL 103 is "rolled up" so that surfaces $111_I$ form the innermost surface of curvature, and surfaces $111_O$ form the outermost surfaces of curvature.

For the avoidance of doubt, it is important to emphasize that although this disclosure has described immediately above (with reference to FIGS. 5 through 11) the optional feature on some MLI embodiments to "convert" between "curved tube" and "straight tube" modes, this disclosure is not limited to such "convertible" embodiments. Other embodiments may be deployed permanently in "curved tube" or "straight tube" modes.

Figure 12:
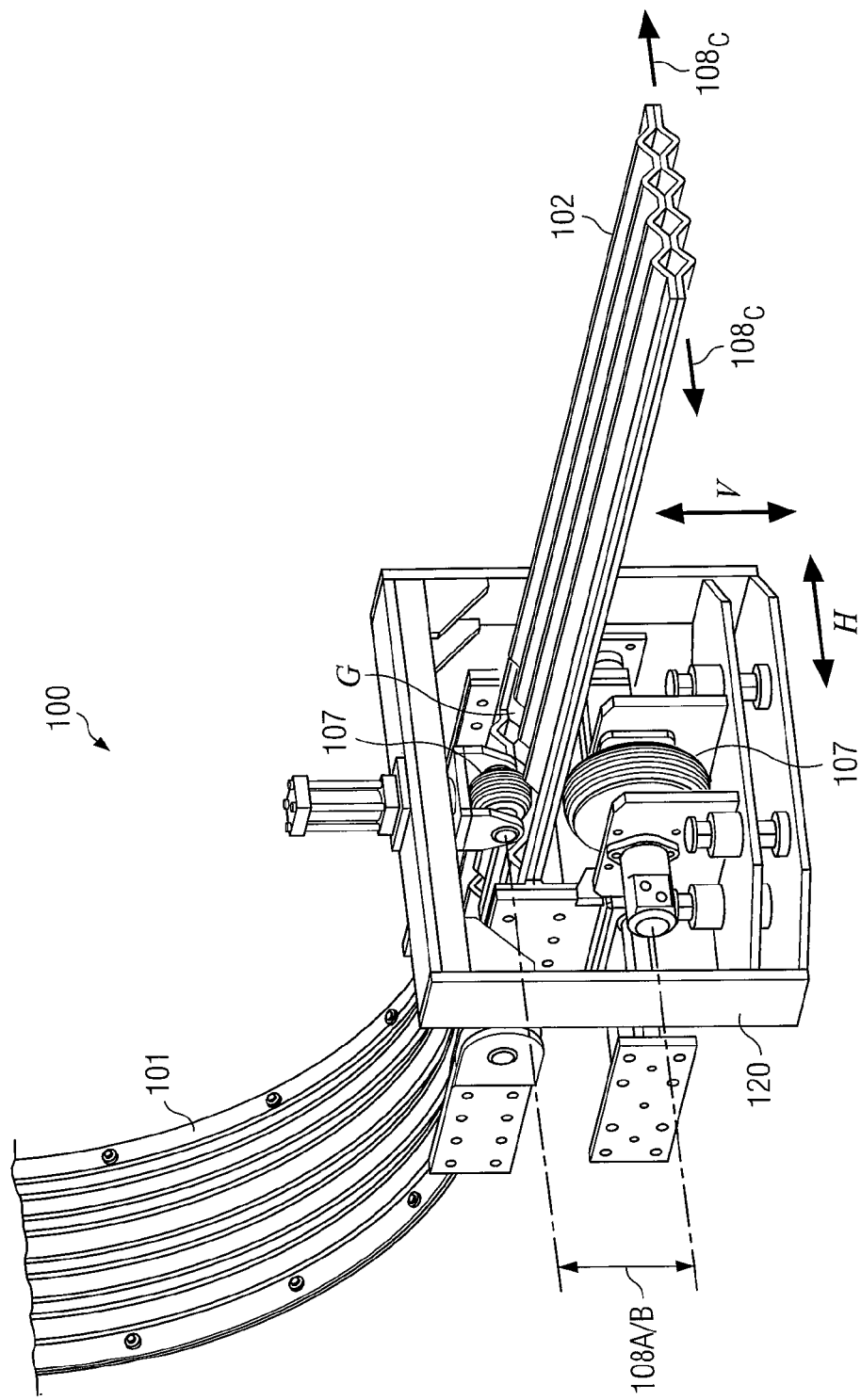
FIGS. 12 and 13 are isometric views illustrating aspects of embodiments of MLI assembly 100 and embodiments of adjustment assembly 120 in more detail.
Figure 13:
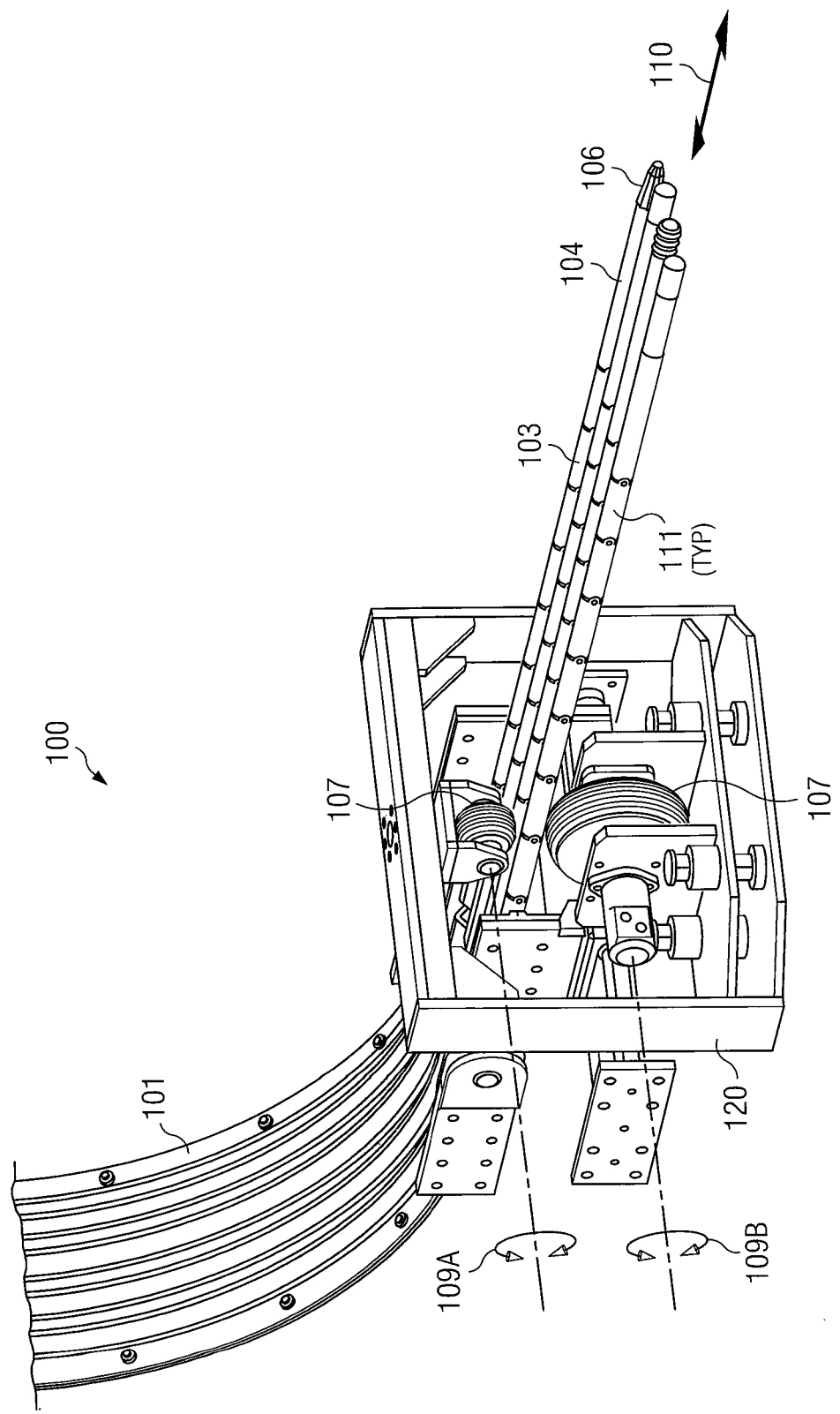

FIGS. 12 and 13 illustrate adjustment assembly 120 (also shown on FIG. 3) in more detail. As before, items shown on FIGS. 12 and 13 that are also shown on any other MLI-series or KJL-series illustration in this disclosure have the same numeral.

The primary difference between FIGS. 12 and 13 is that in FIG. 12, stabbing guide 102 is present, whereas in FIG. 13, it is removed. FIGS. 12 and 13 should be viewed in conjunction with FIGS. 1 and 2.

It will be recalled from earlier disclosure that FIGS. 1 and 2 illustrate, in a functional representation rather that a more scale-accurate representation, the operation of stabbing wheels 107 to enable extension and retraction of KJL 103 into and out of tubular W. FIGS. 1 and 2 further illustrate (again more in a functional sense than in a scale-accurate sense), by means of directional arrows 108A, 108B, 108C, 109A, 109B, 110, H and V, the manner in which stabbing wheels 107 may extend and retract KJL 103, and further, the manner in which MLI 100 may be adjusted positionally (1) to select a particular KJL 103 to be extended and retracted into and out of tubular W, and (2) to set a horizontal and vertical positions of the selected KJL 103 to suit location, diameter and wall thickness of tubular W. FIGS. 12 and 13 illustrate similar disclosure, except in a more scale-accurate representation, and further with reference to adjustment assembly 120.

Looking first at FIG. 12, it will be seen that adjustment assembly 120 comprises stabbing wheels 107. The "treads" of each stabbing wheel 107 will be understood to be engaged, through gaps G in stabbing guide 102, on the outside surface of KJL 103 (hidden from view by stabbing guide 102). Adjustment assembly 120 may move stabbing wheels 107 together and apart in the direction of arrows 108A/B as shown on FIG. 12 in order to engage/disengage KJL 103 through gaps G. Once stabbing wheels 107 are disengaged, adjustment assembly 120 may also move stabbing guide 102 (and connected guide tubes 101) laterally in the direction of arrow 108C in order to bring a selected KJL 103 into position between stabbing wheels 107 for further extension and retraction operations. Further, adjustment assembly 120 may move the entire MLI assembly 100 in this area in the direction of arrows H and V in order to suit location, diameter and wall thickness of a particular tubular W (not illustrated).

The immediately preceding paragraph disclosed that, in accordance with currently preferred embodiments of adjustment assembly 120, lateral movement of stabbing guide 102 enables a selected KJL 103 to be brought into position between stabbing wheels 107. This disclosure is not limited in this regard, however. Other embodiments of adjustment assembly 120 (not illustrated) may move stabbing wheels 107 laterally, or move both stabbing guide 102 and stabbing wheels 107 laterally, in order to bring a selected KJL 103 into position between stabbing wheels 107.

Turning now to FIG. 13, the "treads" of stabbing wheels 107 may now be seen engaged on the outer surface of KJL 103. Adjustment assembly 120 may cause stabbing wheels 107 to rotate in the direction of arrows 109A and 109B in order to extend and retract KJL 103.

It will be appreciated that, with reference to FIGS. 12 and 13, adjustment assembly 120 may be configured to extend or retract KJL assemblies 103 in a range of sizes. In fact, nothing in this disclosure should be interpreted to limit KJL assemblies 103 (and corresponding KJL segments 111) to any particular size or length. While FIGS. 1 and 2 above illustrate a single hose 105 deployed in each KJL 103, it will be appreciated that this disclosure is not limited to any particular number of hoses 105 that may be deployed in a single KJL 103. Multiple hoses 105 may be deployed in any KJL 103, according to user selection and within the capacity of a particular size of KJL 103 to carry such multiple hoses 105.

FIG. 14 illustrates an exemplary suite of 4 (four) KJL segments 111A through 111D in a range of sizes (diameters) and corresponding lengths. Each of KJL segments 111A through 111D conform to the general geometry and general concatenation concepts described above with reference to FIGS. 10 and 11. Although FIG. 14 illustrates individual, single KJL segments 111A-D, it will be appreciated that multiples of each of KJL segments 111A-D may be concatenated into KJL strings that are functionally and operationally equivalent to the KJL assemblies 103 illustrated and described elsewhere in this disclosure.

Earlier disclosure with reference to FIGS. 1 and 2 described generally the concept that multiple hoses 105 may be deployed in a single KJL 103. FIG. 14 shows that as the size (diameter) of KJL segments 111A-D increases, the corresponding internal capacity thereof increases, making a concatenated string thereof increasingly suitable to carry more than one hose 105 (hoses 105 omitted for clarity on FIG. 14).

The Scorpion System MLI contemplates a wide variety of hoses (and corresponding tooling at the distal end thereof) being available to MLI 100 for internal cleaning, inspection, data acquisition and other operations. Exemplary lances in a preferred embodiment are described above. Hoses suitable to serve such lances include (by way of example only, and without limitation): high volume air hoses for pneumatic tooling; high pressure water; steam; high temperature water; and conduits (e.g. pvc plastic) for data lines, electrical power lines, solid conductors, coils or antennae.

KJL 111A on FIG. 14 is illustrated as having the largest size (diameter) of the suite of KJL segments 111A-D. In currently preferred embodiments, KJL 111A is about 4 inches in diameter. This 4-inch diameter allows for an internal diameter with capacity to carry several hoses. The precise number capable of being carried will depend on the user's selection of diameter of hoses.

KJL segments 111B, 111C and 111D are illustrated as progressively smaller in size (diameter) than KJL segment 111A, and will, again dependent on user selection, be capable of carrying correspondingly fewer hoses each.

Generally, users are likely to select KJL size (diameter) according to the tooling intended to be deployed at the distal end of the KJL. Multiple hoses carried by a particular KJL will enable deployment of a multi-tool head at the distal end. Alternatively, multiple hoses carried in a particular KJL may be connected and disconnected to suit tooling at the distal end of the KJL as needed.

In addition to number of hoses, users are further generally likely to select KJL size (diameter) according to the size (diameter) of hose(s) intended to be carried Larger size (diameter) hoses may be preferable in long KJL assemblies in order to mitigate pressure loss and/or flow rate loss over the length of the hose. Similarly, larger size (diameter) conduits may be preferable in long KJL assemblies in order to carry larger diameter cables, which are less susceptible to voltage drop, current losses, or signal losses over greater length.

Further reference to FIG. 14 shows that in preferred embodiments, the length of KJL segments 111A-D changes inversely with respect to the size (diameter). A primary reason, again in preferred embodiments, is manufacturing economy. With reference now to FIG. 7, it will be appreciated that the manufacturing costs of a concatenated KJL assembly 103 for a particular size (diameter) will increase with the number of articulated KJL segments 111 that are deployed in the concatenated string. It is preferable, for manufacturing economy, to make the length of individual KJL segments 111 as long as possible in order to reduce the number of KJL segments 111 that will require concatenation. However, the concatenated string must still be able to be extended and retracted around bend B without undue bending stress.

Referring now to FIG. 14 again, it will be appreciated that the smaller the size (diameter) of KJL segments 111A-D, the more receptive to bending an individual KJL segment is likely to be when a concatenation thereof is extended and retracted around bend B (from FIG. 7). Thus, again in preferred embodiments, such smaller-sized (smaller-diameter) KJL segments may be manufactured with a longer distance between the articulations in a concatenation thereof. Hence such smaller-sized (smaller diameter) KJL segments may be manufactured to be greater in length.

As previously noted, FIG. 14 illustrates an exemplary suite of 4 (four) KJL segments 111A through 111D, in which KJL segments 111A-D decrease in size (diameter) moving from 111A though to 111D, and correspondingly increase in length. Nothing in this disclosure should be interpreted, however, to limit the Scorpion System MLI to such an arrangement. According to user selection and design, a particular deployment of the Scorpion System MLI may have any number of KJL assemblies, in any arrangement of size (diameter) and associated length.

It will be appreciated that when the Scorpion System MLI is configured with a suite of KJL assemblies of differing size (diameter) and corresponding differing KJL segment length, guide tubes 101 and stabbing guide 102 (as illustrated on FIGS. 5 and 6, for example) may become more complex to manufacture, assemble and disassemble. Accordingly, the Scorpion System MLI provides the Multi-Lance Guide (MLG) as an optional, alternative embodiment for such deployments of multi-size KJL assemblies. In such embodiments, the MLG generally substitutes for guide tubes 101 and stabbing guide 102.

FIG. 14 illustrates Multi-Lance Guide (MLG) 150, comprising MLG tube 151 and MLG interior 152. MLG interior 152 provides MLG apertures 153 in corresponding size and number to match concatenated strings of KJL segments 111A through 111D. The diameters of each of MLG apertures 153 are pre-selected to slideably receive their corresponding concatenated string of KJL segments 111A-D, as applicable.

FIG. 15 illustrates MLG 150 where, by comparison to FIGS. 5 and 6, for example, MLG 150 will be seen to be suitable to generally substitute for guide tubes 101 and stabbing guide 102 to hold and guide KJL assemblies 103 (not illustrated on FIG. 15) during extraction and retraction operations. Nothing in this disclosure, however, should be interpreted to require (or favor) an embodiment comprising MLG 150 over an embodiment comprising guide tubes 101 and stabbing guide 102, or vice versa. This disclosure is not limiting in this regard.

As shown on FIG. 15, MLG 150 comprises MLG straight sections $150_S$, MLG curved sections $150_C$ and MLG stabbing guide $150_{SG}$. Each of $150_S$, $150_C$ and $150_{SG}$ further comprise MLG tube 151 and MLG interior 152 (or, more precisely, sections thereof). As noted immediately above with reference to FIG. 14, and as now can be seen further on FIG. 15, MLG interior 152 provides MLG apertures 153 throughout in size and number to slideably receive a corresponding suite of user-selected KJL assemblies 103 (not illustrated on FIG. 15).

FIG. 15 further shows that a plurality of MLG straight sections $150_S$ and MLG curved sections $150_C$ may be concatenated and then joined to MLG stabbing guide $150_{SG}$ to create MLG 150 per user selection and design. Concatenation of straight sections $150_S$ and curved sections $150_C$ (and then to MLG stabbing guide $150_{SG}$) may be by conventional methods, such as (for example) fastening with bolts. Such exemplary concatenation fastening apparatus has been omitted for clarity on FIG. 15 (and on other illustrations in this disclosure) for MLG straight sections $150_S$ and MLG stabbing guide $150_{SG}$, but may be seen on FIG. 15 for MLG curved sections $150_C$.

FIG. 15 further depicts gap G in MLG stabbing guide $150_{SG}$. Referring back momentarily to disclosure associated with FIG. 12, gaps G on top of and underneath MLG stabbing guide $150_{SG}$ (gap G underneath hidden from view on FIG. 15) are operable to allow stabbing wheels 107 (as shown on FIG. 12) to engage KJL assemblies 103 deployed inside MLG stabbing guide $150_{SG}$.

FIG. 15 also illustrates MLG feet 154, whose function is to enable the entire MLG 150 assembly to slide unrestrained over supporting structural steel (omitted for clarity) during Scorpion System MLI operations. It will be recalled from earlier disclosure that preferred embodiments of the Scorpion System MLI enable users to select from among two or more (and preferably four) KJL assemblies in deciding which KJL assembly to extend and retract into a tubular. It will be further recalled from disclosure associated with FIG. 12 that adjustment assembly 120 enables movement in the direction of arrows H, V and 108C in order to position a particular KJL assembly with respect to a tubular. Referring now to FIG. 15 again, it will be appreciated that sliding movement of MLG feet 154 over supporting structural steel (omitted for clarity) enables overall displacement of MLG 150 to accommodate corresponding movement and displacement when a user selects a particular KJL assembly to be positioned for extension/retraction into and out of a tubular (per FIGS. 12 and 13 and associated disclosure). MLG feet 154 may be of any conventional construction, such as (for example) ball bearings or ball races enclosed in metal or plastic housings.

FIGS. 16 and 17 illustrate MLG straight section $150_S$ (from FIG. 15) in greater detail. As also noted above with reference to FIG. 15, conventional structure (such as bolts or other fasteners) disposed to enable concatenation of multiple MLG straight sections $150_S$ has been omitted from FIGS. 16 and 17 for clarity. FIG. 16 illustrates MLG straight section $150_S$ comprising MLG tube 151 encasing MLG interior pieces $152_A$ and $152_B$ (which together comprise MLG interior 152 as illustrated on FIGS. 14 and 15). FIG. 16 also depicts MLG apertures 153, which have been described in greater detail above with reference to FIGS. 14 and 15.

Referring now to FIGS. 16 and 17 together, it will be seen that in currently preferred embodiments, MLG interior pieces $152_A$ and $152_B$ are two mirror-image halves disposed to be joined horizontally to form MLG interior 152. This currently preferred embodiment simplifies the manufacture of MLG interior 152, enabling the fabrication of long, straight sections of MLG interior pieces $152_A$ and $152_B$ that include substantially precise semi-circular cutouts for MLG apertures 153 over the entire length. The need for precise drilling of MLG apertures 153 over the entire length of MLG interior 152 is thus obviated.

In currently preferred embodiments, MLG interior 152 is made of Ultra-High Molecular Weight (UHMW) plastic throughout MLG 150 (including MLG straight sections $150_S$, MLG curved sections $150_C$ and MLG stabbing guide $150_{SG}$). This UHMW plastic material is hard and robust, yet suitable for machining and related operations to create MLG apertures 153 in fully assembled MLG interiors 152. The UHMW plastic material is further low-friction and self-lubricating, and also relatively hard-wearing, enabling KJL assemblies received in MLG apertures 153 to slide operably therethrough during extension and retraction operations.

With further reference to FIGS. 16 and 17, it will be understood that MLG straight sections $150_S$ are assembled by receiving MLG interior pieces $152_A$ and $152_B$ into MLG tube 151. MLG interior pieces $152_A$ and $152_B$ may be secured in MLG tube 151 by conventional methods, such as (for example) bolts, screws or other fasteners. All of such securing structure has been omitted for clarity on FIGS. 16 and 17. However, it will be appreciated that by using fasteners for such securing structure, MLG interior pieces $152_A$ and $152_B$ are interchangeable within MLG tubes 151. MLG interior pieces $152_A$ and $152_B$ may thus be changed out in individual MLG straight sections $150_S$ if they become damaged or worn. Similarly, if the user desires to change the configuration of KJL sizes (diameters) deployed within MLG 150, then MLG interior pieces $152_A$ and $152_B$ may be changed out throughout to provide corresponding receiving MLG apertures 153.

FIGS. 18 and 19 illustrate MLG curved section $150_C$ (from FIG. 15) in more detail. FIG. 19 depicts MLG curved section $150_C$ viewed from the direction of arrow 170 as shown on FIG. 18. The component parts of MLG curved section $150_C$ depicted on FIG. 18 are also depicted on FIG. 19 from this alternative view. It will be seen immediately from FIGS. 18 and 19 that conceptually, with its generally trapezoidal profile, MLG curved section $150_C$ is analogous in form and function to KJL segment 111 as illustrated on FIG. 10. For this reason, it may be helpful to read the following disclosure making reference to FIGS. 18 and 19 in association with earlier disclosure making reference to FIG. 10.

As with KJL segments 111 on FIG. 10, the intent of the generally trapezoidal profile of MLG curved section $150_C$ on FIGS. 18 and 19 is to enable a concatenated string of MLG curved sections $150_C$ to follow a curved path, as illustrated on FIG. 15. Accordingly, with reference to FIG. 18, MLG curved section $150_C$ comprises MLG tube 151 with opposing MLG tube sides $151_I$ and $151_O$. MLG tube side $151_I$ is shorter in longitudinal length than tube side $151_O$ in order to give MLG curved section $150_C$ its generally trapezoidal profile. It will be appreciated that when multiple MLG curved sections $150_C$ are concatenated such that MLG tube sides $151_I$ mate together and tube sides $151_O$ mate together, a generally curved string thereof will result, as illustrated on FIG. 15.

Concatenation of MLG curved sections $150_C$ may be enabled by any suitable conventional structure. In currently preferred embodiments, as illustrated on FIGS. 18 and 19, each MLG curved section $150_C$ provides MLG concatenation bolts 155, MLG concatenation holes 156 and MLG concatenation lugs 157. Concatenation is enabled in such embodiments by fastening the MLG concatenation bolts 155 through the MLG concatenation lugs 157 of a first MLG curved section $150_C$ and into the MLG concatenation holes 156 of a second, neighboring MLG curved section $150_C$. Nothing in this disclosure should be construed, however, as limiting the concatenation of MLG curved sections $150_C$ to the use of concatenation bolts, lugs and holes as illustrated on FIGS. 18 and 19.

The actual overall size and trapezoidal profile dimensions of MLG curved sections $150_C$ (and, indeed, the corresponding dimensions of MLG straight sections $150_S$ and MLG stabbing guide $150_{SG}$) are all per user selection and design, according to the needs of a particular Scorpion System MLI (and associated MLG) deployment. Nothing herein should be construed to limit the Scorpion System to (or favor) a particular dimensional MLG design.

FIGS. 18 and 19 also illustrate currently preferred embodiments of MLG interior 152 for MLG curved section $150_C$. As with MLG straight section $150_S$ (described above with reference to FIGS. 16 and 17), MLG tube 151 for MLG curved section $150_C$ on FIG. 18 encases MLG interior 152. MLG interior 152 on FIG. 18 thus shares the general trapezoidal profile of MLG curved section $150_C$ and associated MLG tube 151. In distinction to MLG straight section $150_S$ (described above with reference to FIGS. 16 and 17), however, FIGS. 18 and 19 show that currently preferred embodiments call for the manufacture of MLG interior 152 for MLG curved section $150_C$ from one solid piece of UHMW plastic, and further call for MLG apertures 153 provided in MLG interior 152 to be oblate or slotted rather than substantially circular.

By momentary reference to FIG. 15, it will be appreciated that the shorter overall longitudinal length of a typical MLG curved section $150_C$ enables MLG interior 152 to be manufactured from one UHMW plastic piece, since MLG apertures 153 may be more precisely drilled, reamed and otherwise machined through such a shorter length of UHMW plastic. It will be further appreciated by reference to FIGS. 18 and 19 that MLG apertures 153 are oblate or slotted in MLG curved section $150_C$ in order to accommodate the articulated series of straight edges that occurs when KJL assemblies deployed within MLG apertures 153 are in "curved tube" mode, per earlier disclosure making reference to FIGS. 8 and 11.

It will be further recalled from FIG. 14 and associated disclosure that in currently preferred embodiments, smaller diameter KJL assemblies are preferably manufactured with longer longitudinal length in order to optimize manufacturing costs. It will thus be appreciated that when such smaller-diameter, longer-longitudinal-length KJL assemblies are in "curved tube" mode (per FIGS. 8 and 11 and associated disclosure), the resulting articulated series of straight edges is more pronouncedly "straight" (i.e. more a series of straight edges and less of a "curve"). This "more pronounced straight edge" effect in turn requires a correspondingly greater "slotting" of the MLG apertures 153 in MLG curved sections 150, in order to slideably accommodate the straight edges of a KJL assembly in "curved tube" mode without undue bending.

It will be again understood that actual oblate or slotted dimensions of MLG apertures 153 in MLG curved sections $150_C$ are all per user selection and design, according to the needs of a particular deployment of KJL assemblies therein, in combination with the overall dimensional design of the MLG. Nothing herein should be construed to limit the MLG in this regard.

It will be further understood that MLG interior 152 may be secured in MLG tube 151 on MLG curved sections 150C by conventional methods, such as (for example) bolts, screws or other fasteners. All of such securing structure has been omitted for clarity on FIGS. 18 and 19. However, it will be appreciated that by using fasteners for such securing structure, MLG interiors 152 are interchangeable within MLG tubes 151. MLG interiors 152 may thus be changed out in individual MLG curved sections $150_C$ if they become damaged or worn. Similarly, if the user desires to change the configuration of KJL sizes (diameters) deployed within MLG 150, then MLG interiors 152 may be changed out throughout to provide corresponding receiving MLG apertures 153.

Figure 21:
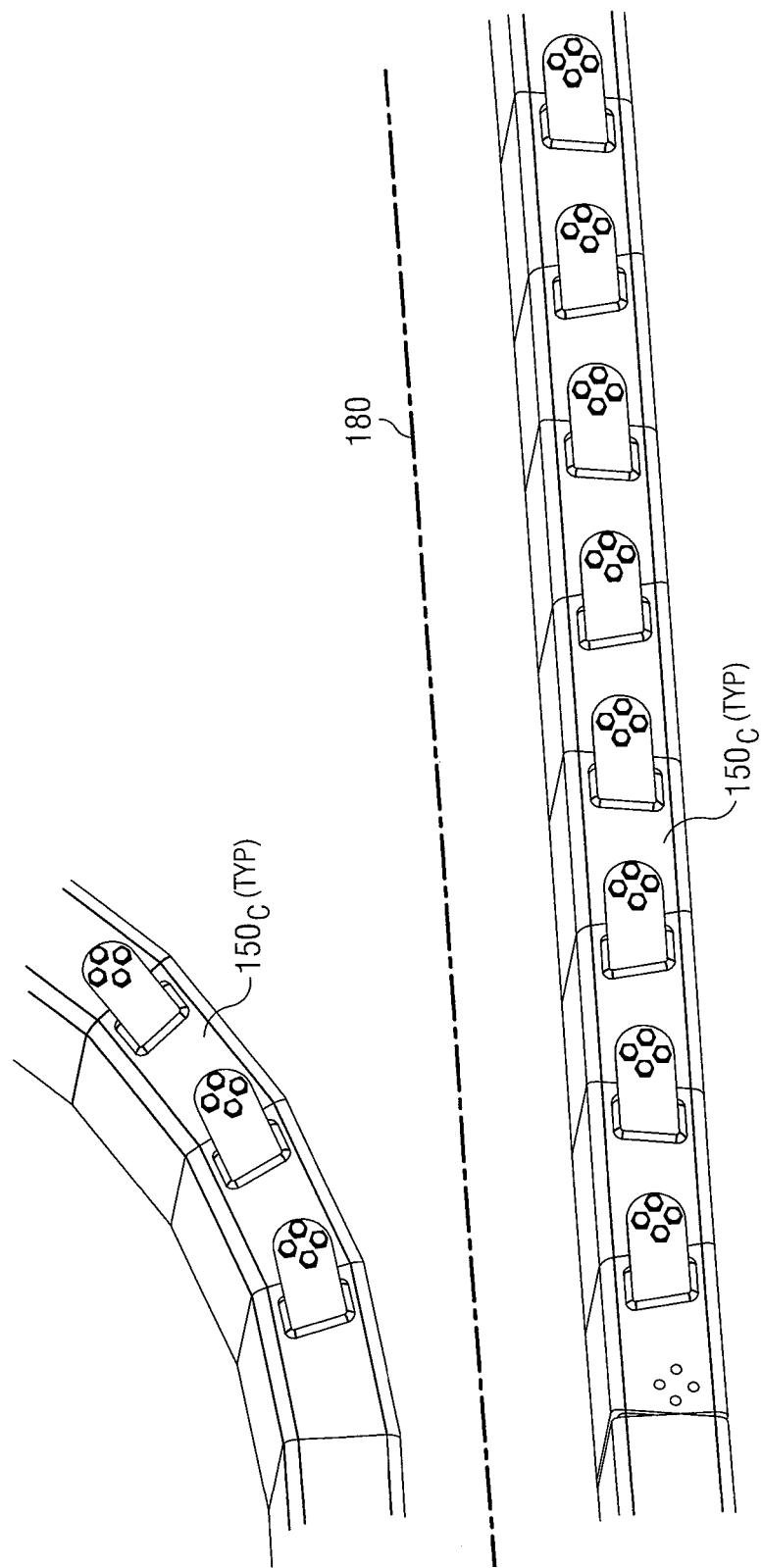

FIGS. 20 and 21 are side-by-side comparisons of MLG 150 in "curved tube" and "straight tube" modes. Earlier material in this disclosure (for example, with reference to FIGS. 7 through 11) describes embodiments of the Scorpion System MLI in "curved tube" and/or "straight tube" modes, according to user selection Such material further describes embodiments in which KJL assemblies may be "converted" back and forth between "curved tube" and "straight tube" modes. FIGS. 20 and 21 illustrate "curved tube" and "straight tube" embodiments of MLG 150, which may also be converted back and forth between modes in order to support the corresponding mode that the user selects for KJL assemblies deployed therein.

FIG. 21 is an enlargement of a portion of FIG. 20 as shown on FIG. 20. Chained line 180 appears in both FIGS. 20 and 21, and serves to divide the illustrations functionally between "curved tube" mode (above chained line 180) and "straight tube" mode (below chained line 180).

Referring first to FIG. 20, MLG 150 is illustrated in "curved tube" mode (above chained line 180) substantially as illustrated in FIG. 15. In this "curved tube" mode, MLG 150 comprises MLG straight sections $150_S$, MLG curved sections $150_C$ and MLG stabbing guide $MLG_{SG}$, as previously illustrated. Further, MLG curved sections $150_C$ have been concatenated as described above with reference to FIGS. 18 and 19, wherein the general trapezoidal profiles of MLG curved sections $150_C$ are aggregated into an overall generally curved concatenation thereof.

FIG. 20 also illustrates MLG 150 in "straight tube" mode (below chained line 180). Again, MLG 150 comprises MLG straight sections $150_S$, MLG curved sections $150_C$ and MLG stabbing guide $MLG_{SG}$ in this "straight tube" mode. However, in this "straight tube" mode, MLG curved sections $150_C$ have been concatenated such that their general trapezoidal profiles have been arranged to "cancel each other out" rather aggregate into an overall general curve.

This "canceling out" aspect of a "straight tube" embodiment of MLG 150 is best viewed on FIG. 21. Above chained line 180, FIG. 21 illustrates the general trapezoidal profiles of MLG curved sections $150_C$ arranged to aggregate into an overall general curve. Below chained line 180, FIG. 21 illustrates the general trapezoidal profiles of MLG curved sections $150_C$ arranged to oppose, or to "cancel each other out", so that the concatenation of MLG curved sections $150_C$ is in a straight line.

It thus will be appreciated that a concatenation of MLG curved sections $150_C$ may be "converted" back and forth between "curved tube" and "straight tube" modes by unfastening the concatenated sections, reversing the general trapezoidal aspect of every other section (i.e. "flipping it over"), and re-fastening. In such "convertible" embodiments, fastening structure should preferably be provided symmetrically to enable similar fastening whether in "curved tube" or "straight tube" modes. Also, with additional reference to FIGS. 18 and 19, before MLG curved sections $150_C$ are re-fastened, MLG interiors 152 of MLG curved sections $150_C$ that are reversed (or "flipped over") may also need to be reversed (or "flipped over") themselves in order to preserve continuity of MLG apertures 153 from one MLG curved section $150_C$ to the next. It will be seen from FIGS. 18 and 19 that reversal of MLG interiors 152 may be accomplished by unfastening and removing them from their MLG tubes 151, reversing their orientation, and then re-fastening them into MLG tubes 151.

Although not illustrated in any detail, it will be understood from FIG. 15 that MLG stabbing guide $150_{SG}$ is, in currently preferred embodiments, substantially a MLG straight section $150_S$ as illustrated and described in detail with reference to FIGS. 16 and 17. MLG stabbing guide $150_{SG}$ differs primarily from MLG straight section $150_S$ in that MLG stabbing guide $150_{SG}$ also provides gaps G (as described with reference to FIG. 15).

FIGS. 22 through 25 illustrate various views of Single Lance Reel (SLR) assembly $190_S$ and Multi-Lance Reel (MLR) assembly $190_M$. FIG. 26 illustrates aspects and features of MLR axle assembly $193_M$ on MLR assembly $190_M$ in more detail. As throughout this disclosure, items depicted on FIGS. 22 through 26 that are also depicted on other FIGURES in this disclosure have the same numeral.

Embodiments of the Scorpion System deploying either SLR assembly $190_S$ or MLR assembly $190_M$ on FIGS. 22 through 25 enable concatenated strings of KJL assemblies 103 to be rolled and unrolled, as required, onto or off a rotary "reel"-like assembly as such. KJL assemblies 103 are selectably retracted or extended in and out of tubular W. It will be appreciated the primary difference between SLR assembly $190_S$ and MLR assembly $190_M$ is that SLR assembly $190_S$ provides "reel"-like structure for rolling up and unrolling a single KJL assembly 103, while MLR assembly $190_M$ provides "reel"-like structure for rolling up and unrolling multiple KJL assemblies 103 (each KJL assembly 103 capable of being rolled up or unrolled independently per user selection). FIGS. 22 through 26 illustrate embodiments of MLR assembly $190_M$ in which an example of four (4) KJL assemblies 103 are available to be independently rolled up or unrolled. Nothing in this disclosure should be interpreted, however, to limit MLR assembly $190_M$ to handling any particular number (two or more) of KJL assemblies 103.

SLR assembly $190_S$ and MLR assembly $190_M$ are thus alternative embodiments to the earlier described functionality provided by MLG 150 (as illustrated on FIGS. 14 through 21), or guide tubes 101 (as illustrated on FIGS. 1 through 13). Instead of holding and positioning concatenated strings of KJL assemblies 103 in an encased structure (as in MLG 150 or guide tubes 101), SLR assembly $190_S$ and MLR assembly $190_M$ hold and position concatenated strings of KJL assemblies 103 by rolling them up onto a "reel"-like structure. As will be appreciated from FIGS. 22 through 25, therefore, embodiments deploying either SLR assembly $190_S$ or MLR assembly $190_M$ obviate any need for "curved tube" and "straight tube" modes (such as were described above with reference to MLG 150 or guide tubes 101). In this way, embodiments deploying either SLR assembly $190_S$ or MLR assembly $190_M$ potentially permit substantial savings in footprint. Such SLR and MLR embodiments further simplify overall deployment of the Scorpion System by obviating the structural steel and other conventional infrastructure that, as described above (although not illustrated for clarity), is required to support and serve either MLG 150 or guide tubes 101.

Figure 22:
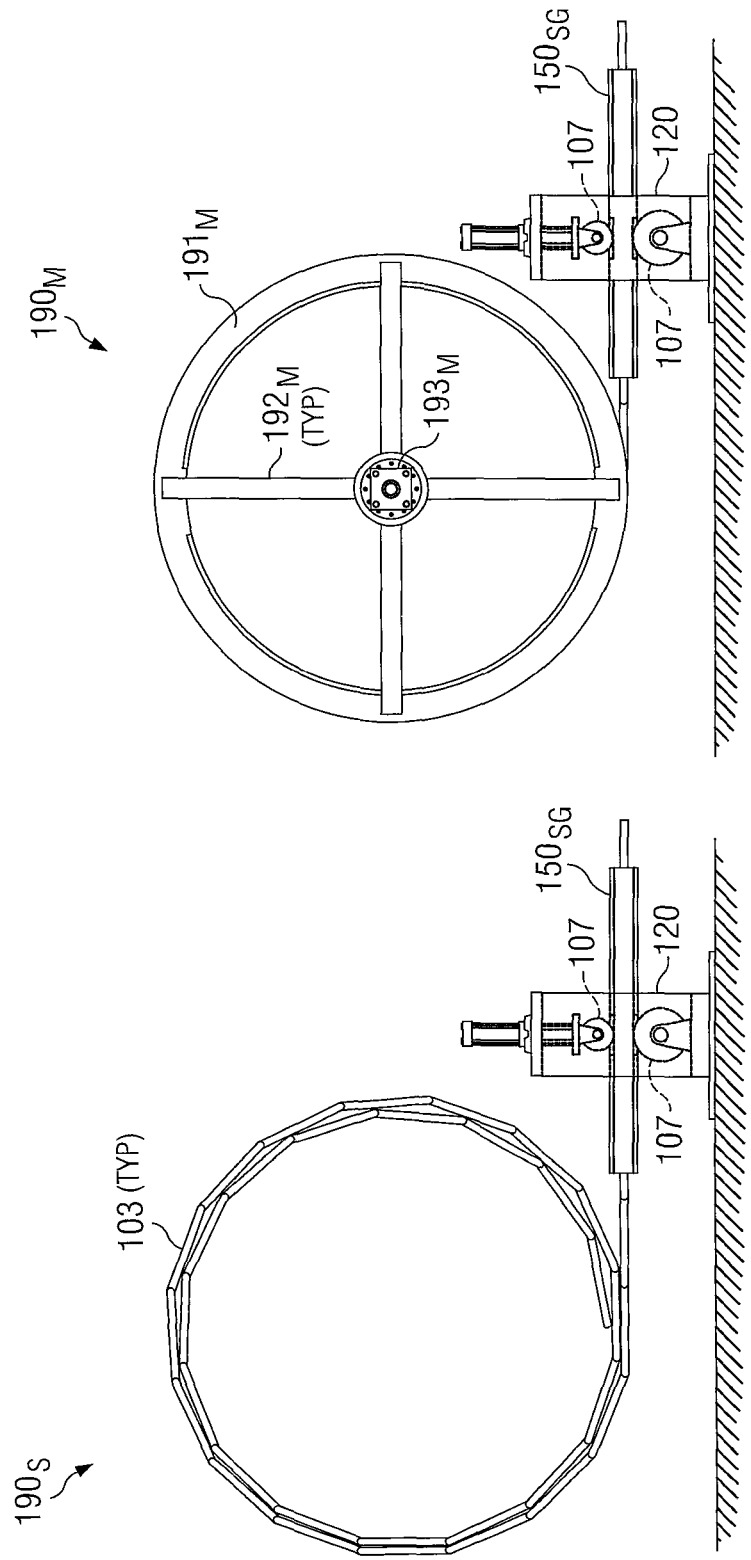
FIG. 22 is an elevation view of embodiments of SLR assembly $190_S$ and MLR assembly $190_M$.

Turning first to FIG. 22, SLR assembly $190_S$ is illustrated with a concatenated string of KJL assemblies 103 substantially fully "rolled up" ready for extension thereof during internal cleaning, inspection or other operations. Substantially all of the structure of SLR assembly $190_S$ has been removed for clarity on FIG. 22 in order to enable better appreciation of the functional operation of SLR assembly $190_S$ (and, by association, MLR assembly $190_M$). The embodiment of SLR assembly $190_S$ illustrated on FIG. 22 further shows depicts an embodiment of MLG stabbing guide $150_{SG}$ (refer FIG. 15) and an embodiment of adjustment assembly 120 (including stabbing wheels 107, hidden from view, refer FIGS. 12 and 13) positioned and disposed, per earlier disclosure, to extend and retract the concatenated string of KJL assemblies 103. It will be understood from the embodiment of SLR assembly $190_S$ illustrated on FIG. 22 that as stabbing wheels 107 on adjustment assembly 120 rotate and extend/retract KJL assemblies 103, the "reel"-like structure provided by SLR assembly $190_S$ (omitted for clarity on FIG. 22 but depicted, for example, on FIG. 23) unrolls and rolls up in corresponding fashion to "pay out" and "take up" the concatenated string of KJL assemblies 103.

FIG. 22 further illustrates MLR assembly $190_M$, which, as noted, operates in conceptually and functionally the same manner as SLR assembly 190S to "pay out" and "take up" any one of multiple concatenated strings of KJL assemblies 103 deployed thereon as such KJL assemblies 103 are extended/retracted independently per user selection. The embodiment of MLR assembly $190_M$ depicted on FIG. 22 is hiding the KJL assemblies 103 deployed thereon, but these KJL assemblies 103 may be seen by momentary reference to, for example, the view on FIG. 24. The embodiment of MLR assembly $190_M$ depicted on FIG. 22 illustrates MLR rim $191_M$, MLR spokes $192_M$ and MLR axle assembly $193_M$ in elevation view and in general form.

Figure 23:
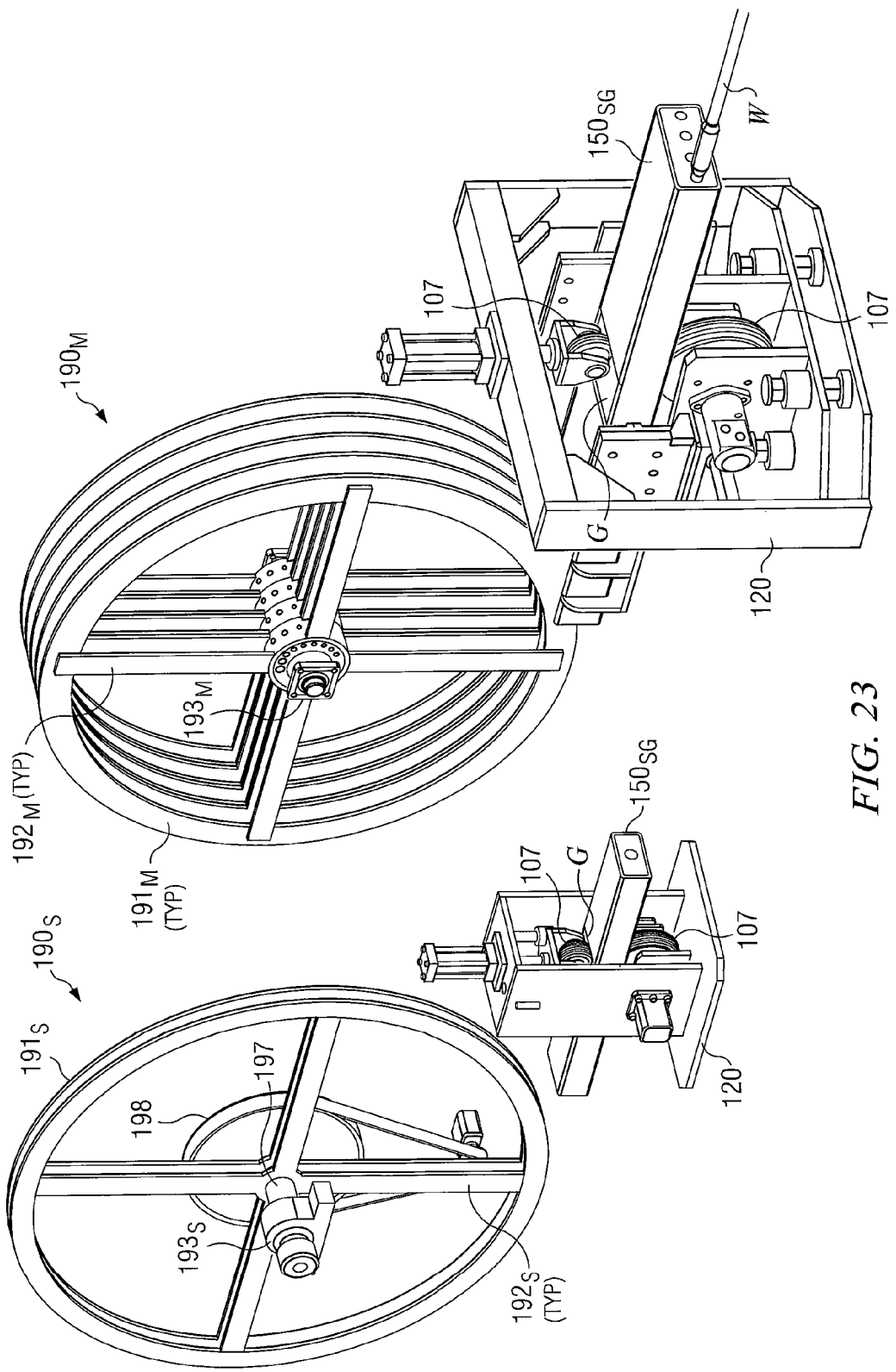
FIGS. 23, 24 and 25 are isometric views of embodiments of SLR assembly $190_S$ and MLR assembly $190_M$.

Reference is now made to FIG. 23, depicting SLR assembly $190_S$ and MLR assembly $190_M$ in a perspective view. KJL assemblies 103 (shown on 24 and 22, for example) have been omitted from SLR assembly $190_S$ and MLR assembly $190_M$ on FIG. 23 for clarity. Among other features, FIG. 23 contrasts the multiple independent reel structure of MLR assembly $190_M$ with the single reel structure of SLR assembly $190_S$. FIG. 23 also illustrates each of MLR assembly $190_M$ and SLR assembly $190_S$ having rims $191_M$ and $191_S$, spokes $192_M$ and $192_S$, and axle assemblies $193_M$ and $193_S$ (which features will be described in more detail further on in this disclosure).

In both MLR assembly $190_M$ and SLR assembly $190_S$ embodiments illustrated on 23, wheels 107 engage on KJL assemblies 103 via gap G in embodiments of MLG stabbing guide $150_{SG}$ (KJL assemblies 103 omitted on FIG. 23 for clarity, as noted above). Consistent with earlier disclosure associated with, for example, FIG. 1, rotation of wheels 107 causes KJL assemblies 103 to extend and retract into and out of tubular W. It will be understood from FIG. 22 and now FIG. 23 that as KJL assemblies 103 extend and retract into and out of tubular W, MLR and SLR assemblies $190_M$ and $190_S$ "pay out" and "take up" the concatenated string of KJL assemblies 103 using "reel"-like structure on which KJL assemblies 103 are unrolled and rolled up.

It will be further appreciated with reference to FIG. 23 that on MLR assembly $190_M$, any selected one of the multiple strings of KJL assemblies 103 deployed thereon may be "paid out" and "taken up" independently of the other strings of KJL assemblies 103 also deployed thereon (such non-selected strings of KJL assemblies 103 remaining motionless while the selected one is "paid out" and/or "taken up"). MLR axle assembly $193_M$, in conjunction with MLR rims $191_M$ and MLR spokes $192_M$, provides structure to enable independent "paying out" or "taking up" of any string of KJL assemblies 103 deployed, and will be described in greater detail further on with reference to FIG. 26. This structure on MLR assembly $190_M$ enabling independent "paying out" or "taking up" of any string of KJL assemblies 103 deployed thereon enables MLR assembly $190_M$ to be compatible with earlier disclosure (see FIGS. 1, 2, 12 and 13 and associated disclosure including stabbing wheels 107 and adjustment assembly 120, for example) in which any one of multiple strings of KJL assemblies 103 may be user-selected at any particular time for extension into and retraction out of tubular W. It will be further understood that particularly with regard to MLR assembly $190_M$, as adjustment assembly 120 moves concatenated strings of KJL assemblies 103 from side to side to bring a selected string thereof between stabbing wheels 107, MLR assembly $190_M$ may be disposed to make corresponding lateral movements.

Figure 24:
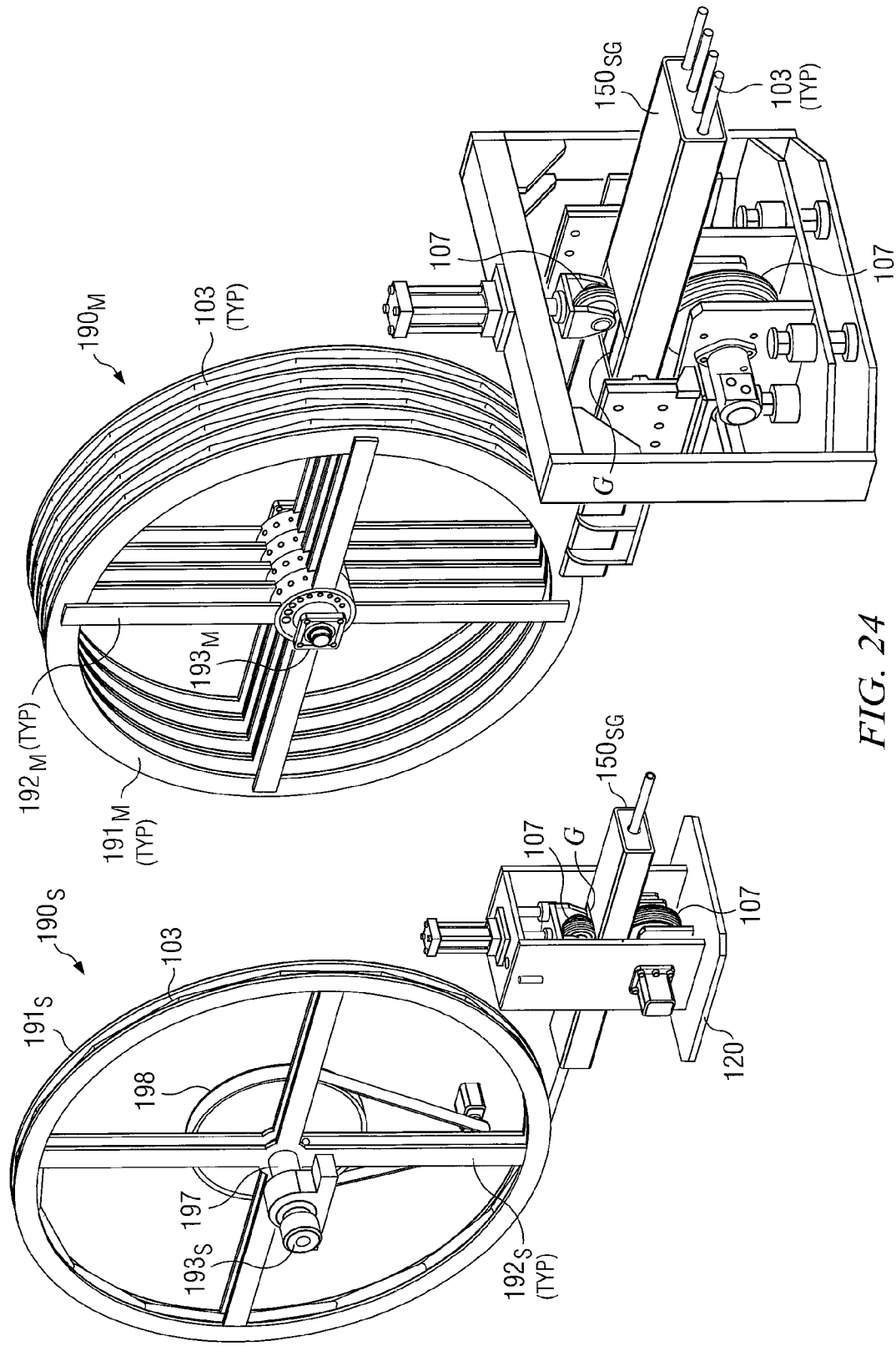

FIG. 24 illustrates MLR and SLR assemblies $190_M$ and $190_S$ in similar fashion to FIG. 23, except enlarged and shown from a different perspective angle. FIG. 24 also shows concatenated strings of KJL assemblies 103 deployed on MLR and SLR assemblies $190_M$ and $190_S$ (such strings of KJL assemblies 103 omitted for clarity on FIG. 23). Disclosure above referring to FIGS. 22 and 23 applies equally with reference to FIG. 24.

Figure 25:
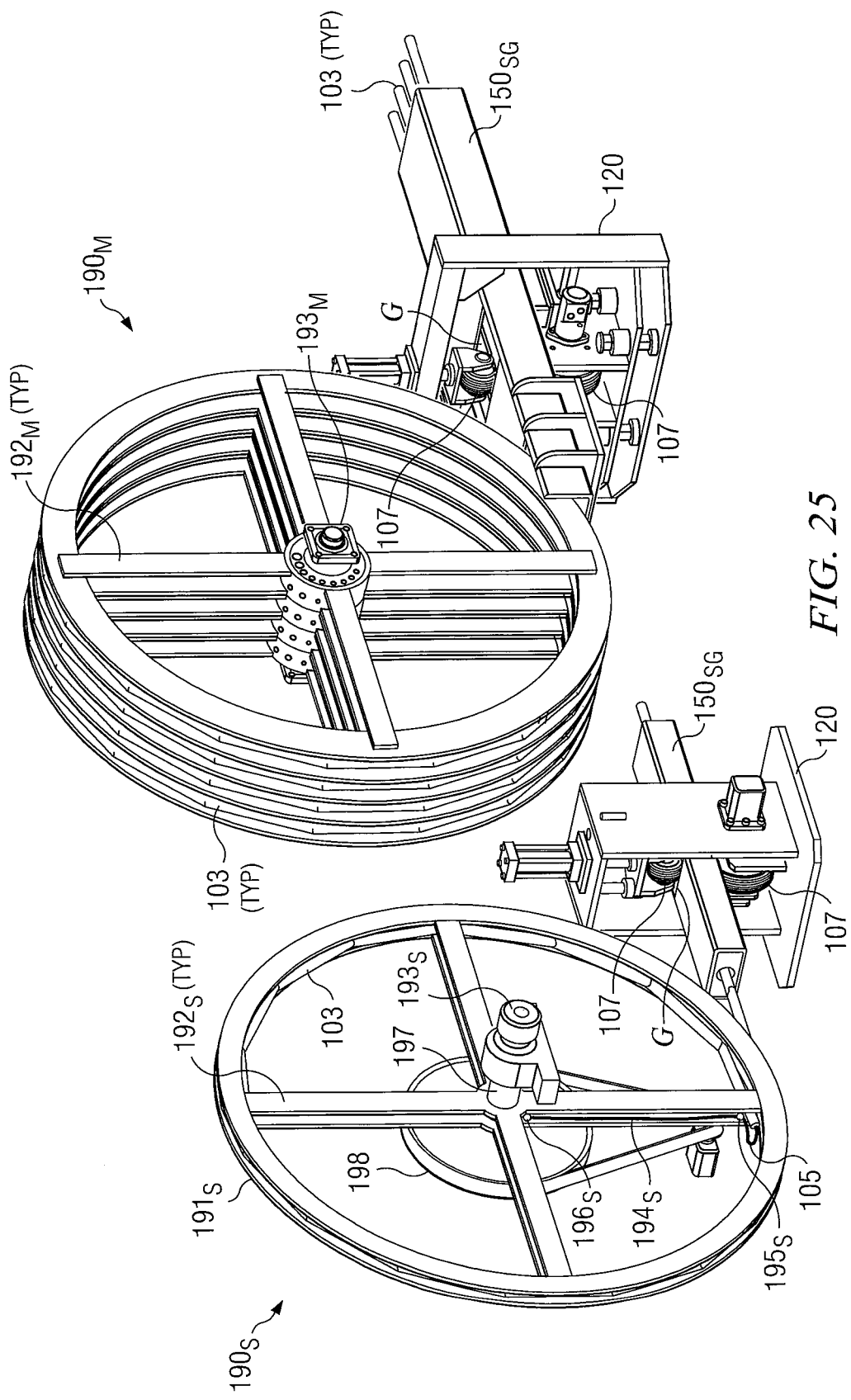
Figure 26:
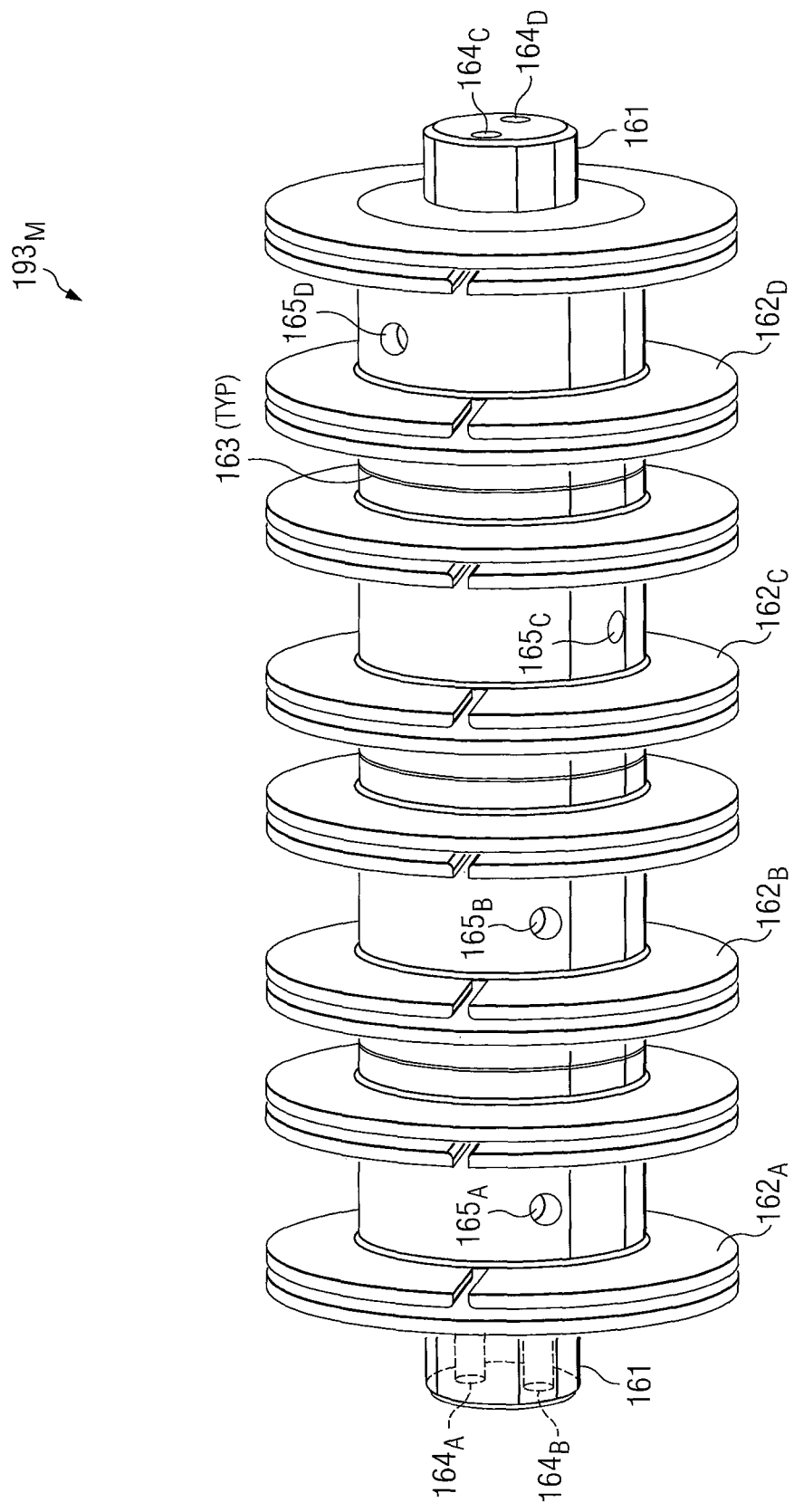
FIG. 26 is an isometric view of aspects of an embodiment of MLR axle assembly $193_M$.

FIG. 25 illustrates MLR and SLR assemblies $190_M$ and $190_S$ in similar fashion to FIG. 24, except shown from a different perspective angle. FIG. 25 further shows SLR assembly $190_S$ with parts of SLR rim $191_S$ removed so that KJL assemblies 103 can be seen more clearly deployed thereon.

The following disclosure regarding deployment of KJL assemblies 103 on SLR rim $191_S$ is also illustrative of corresponding deployment of each of the multiple KJL assemblies 103 acting independently on MLR rims $191_M$, although such structure on MLR rims $191_M$ is hidden from view on FIG. 25. It will be seen on FIG. 25 that the first KJL assembly 103 in the concatenated string thereof is anchored to SLR rim $191_S$ with the distal end of the first KJL assembly 103 near any one of SLR spokes $192_S$. Anchoring may be by any conventional removable anchoring structure, such as threaded bolts, for example, wherein KJL assemblies 103 may be periodically removed from SLR rim $191_S$ for maintenance. In preferred embodiments, SLR rim $191_S$ provides sidewalls whose spacing is selected to be wide enough to enable a string of KJL assemblies 103 to roll up and unroll comfortably between the sidewalls to permit a helical spooling. In this way, unwanted bending, twisting or shear stresses on the couplings between individual KJL assemblies 103 are minimized as strings thereof are rolled up and unrolled. Other embodiments may provide SLR rim $191_S$ to be narrow enough for successive rolls of KJL assemblies 103 to stack vertically on top of each other rather than "sliding down" partially or completely side by side Preferred embodiments of SLR assembly $190_S$ and MLR assembly $190_M$ as illustrated on FIG. 25 are advantageously sized so that approximately two (2) revolutions thereof will extend a string of KJL assemblies 103 from "fully rolled up"

to "fully paid out" (and vice versa). Nothing in this disclosure should be interpreted, however, to limit the choice of size of SLR assembly $190_S$ and/or MLR assembly $190_M$ in this regard.

As noted above, it will be understood that, although not fully depicted on FIG. 25 (because MLR rims $191_M$ on MLR assembly $190_M$ are not partially removed on FIG. 25), the preceding disclosure regarding KJL assemblies 103 deployed on SLR assembly $190_S$ as shown on FIG. 25 is illustrative of each of the KJL assemblies 103 deployed on MLR assembly $190_M$.

It will be further recalled from earlier disclosure that in preferred embodiments, KJL assemblies 103 encase at least one hose 105 that serves tooling head 106 on a distal end of each string of KJL assemblies 103. Refer back, for example, to FIGS. 1 and 14 with associated disclosure herein. Referring now to FIG. 25 again, it will be appreciated that in the illustrated embodiment, hose(s) 105 within KJL assemblies on SLR assembly $190_S$ terminate at SLR rim $191_S$. SLR spoke hose(s) $194_S$ connect to hose(s) 105 at SLR rim hose connection $195_S$ and extend along a selected SLR spoke $192_S$ to SLR axle hose connection $196_S$ near or on SLR axle assembly $193_S$.

It will be further appreciated that preferred embodiments of SLR assembly $190_S$ provide connection structure as described above and illustrated on FIG. 25 (including SLR rim hose connection $195_S$, SLR spoke hose(s) $194_S$ and SLR axle hose connection $196_S$) in order to facilitate maintenance and replacement of hose(s) 105 in KJL assemblies 103. Nothing in this disclosure should be interpreted to limit the type, location or manner of connection of hose(s) 105 across SLR assembly $190_S$ in other embodiments thereof.

With continuing reference to FIG. 25, SLR axle assembly $193_S$ comprises a conventional rotary union 197. A remote source or reservoir of fluids or other material to be carried and ultimately delivered by hose(s) 105 within KJL assemblies 103 may thus be connected to rotary union 197 on SLR axle assembly $193_S$ (such remote source/reservoir and connection omitted on FIG. 25 for clarity). The fluids or other material flow through rotary union 197 and into hose(s) 105 within KJL assemblies 103 via SLR axle hose connection $196_S$, SLR spoke hose(s) $194_S$ and SLR rim hose connection $195_S$.

FIG. 25 further illustrates SLR drive 198 on SLR assembly $190_S$. SLR drive 198 may be any conventional drive mechanism, and this disclosure is not, limited in this regard. In presently preferred embodiments of SLR assembly $190_S$, SLR drive 198 is a direct drive.

SLR drive 198 is provided on SLR assembly $190_S$ to cooperate with stabbing wheels 107 in extending and retracting strings of KJL assemblies 103. In preferred embodiments, stabbing wheels 107 are the primary extending and retraction mechanism (see, for example, FIG. 1 and associated disclosure above). In embodiments deploying SLR assembly $190_S$, however, SLR drive 198 assists stabbing wheels 107 to keep mild tension in strings of KJL assemblies 103 as they are "rolled up" and "paid out". SLR drive 198 may also provide additional power to assist stabbing wheels 107 with extension and retraction of KJL assemblies 103 when required.

It will be recalled from earlier disclosure that FIG. 25 shows SLR assembly $190_S$ with parts of SLR rim $191_S$ removed so that KJL assemblies 103, hose(s) 105 and associated structure can be seen more clearly deployed thereon. The preceding disclosure regarding deployment of KJL assemblies 103 on SLR rim $191_S$ and the structure connecting hose(s) 105 to SLR axle assembly $193_S$ is also illustrative of corresponding deployment of each of the multiple KJL assemblies 103 and associated hoses 105 acting independently on MLR rims $191_M$, although such structure on MLR rims $191_M$ is hidden from view on FIG. 25. In preferred embodiments of MLR assembly $190_M$, although not specifically illustrated, each string of KJL assemblies 103 terminates near a selected MLR spoke $192_M$. Although again hidden from view, it will be understood that hose(s) 105 deployed within each string of KJL assemblies 103 are advantageously connected to MLR axle assembly $193_M$ via MLR rim hose connections, MLR spoke hoses and MLR axle hose connection.

It will be further appreciated that, consistent with similar disclosure with respect to SLR assembly $190_S$ above, preferred embodiments of MLR assembly $190_M$ provide connection structure as described immediately above (including MLR rim hose connections, MLR spoke hoses and MLR axle hose connection identified above but hidden from view on FIG. 25) in order to facilitate maintenance and replacement of hose(s) 105 in KJL assemblies 103. Nothing in this disclosure should be interpreted to limit the type, location or manner of connection of hose(s) 105 across MLR assembly $190_M$ in other embodiments thereof.

FIG. 26 illustrates features and components of an embodiment of MLR axle assembly $193_M$ in more detail. By way of background, it will be appreciated from earlier disclosure that on MLR assembly $190_M$, each string of KJL assemblies 103 deployed thereon is free to be "paid out" or "taken up" independently according to user selection. It will be further recalled that in preferred embodiments (as illustrated on FIG. 25, for example) four (4) independent strings of KJL assemblies 103 are deployed on a single MLR assembly $190_M$. A conventional rotary union, such as rotary union 197 disclosed above on SLR axle assembly $193_S$, is thus not operable for analogous deployment on MLR axle assembly $193_M$, since up to four (4) independent supplies of fluids or other materials need to be carried independently and separately from their respective remote sources or reservoirs via MLR axle assembly $193_M$ to a corresponding hose 105 within one of the independently extensible/retractable strings of KJL assemblies 103 deployed on MLR assembly $190_M$. A conventional rotary union will typically provide structure for only a single supply of fluid through the union.

FIG. 26 illustrates aspects of MLR axle assembly $193_M$ in which, consistent with preferred embodiments illustrated elsewhere in this disclosure, four (4) separate and independent supplies of fluids or other materials may be carried through MLR axle assembly $193_M$. As noted earlier, this disclosure's example to illustrate and describe MLR assembly $190_M$ (and associated MLR axle assembly $193_M$) as providing four (4) separate and independent supplies of fluids or other materials to each of four (4) independently-operable strings of KJL assemblies 103 is an exemplary embodiment only. Nothing in this disclosure should be interpreted to limit MLR assembly $190_M$ (and MLR axle assembly $193_M$) to provide for more or fewer than four (4) separate and independently-operable strings of KJL assemblies 103.

With continuing reference to FIG. 26, MLR axle assembly $193_M$ comprises stationary axle 161, on which four (4) axle spools $162_A$, $162_B$, $162_C$ and $162_D$ are separated by spool seals 163. Spool seals 163 may be any suitable seal between independently rotating parts, such as conventional swivel seals, and this disclosure is not limited in this regard. Axle spools $162_A$, $162_B$, $162_C$ and $162_D$ are each free to rotate separately and independently on axle 161. Viewing FIGS. 22 and 26 together, it will be appreciated that MLR spokes $192_M$ on FIG. 22 advantageously attach to MLR axle assembly $193_M$ via bolting or other similar conventional means to axle spools $162_A$, $162_B$, $162_C$ and $162_D$, as illustrated on FIG. 26.

Referring again to FIG. 26, axle 161 further comprises inlet ports $164_A$ and $164_B$ at one end, and inlet ports $164_C$ and $164_D$ at the other end. Axle spools $162_A$, $162_B$, $162_C$ and $162_D$ each provide a corresponding outlet port $165_A$, $165_B$, $165_C$ and $165_D$. Inlet ports $164_A$ through $164_D$ each connect to a corresponding one of outlet ports $165_A$ through $165_D$ via individual and separate pathways through the interior of axle 161 and axle spools $162_A$ through $162_D$, respectively (such pathways not illustrated). Such pathways may be of any convenient conventional design, such as drilling out each pathway in the core of axle 161 beginning at an inlet port $164_A$ through $164_D$, and emerging in a radial direction at the circumference of axle 161 in line with the circumference of rotation above of the corresponding outlet port $165_A$ through $165_D$ on axle spools $162_A$ through $162_D$. Each axle spool $162_A$ through $162_D$ may then provide a semi-circular (or other shaped profile) groove on its internal circumference in line with its corresponding outlet port $165_A$ through $165_D$, and to which groove each corresponding outlet port $165_A$ through $165_D$ is connected. Such connection may, in some embodiments, include a semi-circular (or other shaped profile) annular groove around the outer circumference of axle 161 that coincides with the grooves on the internal circumference of axle spools $162_A$ through $162_D$ under outlet ports $165_A$ through $165_D$. In such embodiments, the grooves on each surface (outer surface of axle 161 and internal surface of axle spools $162_A$ through $162_D$) may combine to form a ring groove as part of the flow passageway between inlet ports $164_A$ through $164_D$ and corresponding outlet ports $165_A$ through $165_D$. Rotary seals may be provided between axle 161 and axle spools $162_A$ through $162_D$ either side of the groove. In this way, fluids or other material may enter into a selected one of inlet ports $164_A$ through $164_D$ and exit out of a corresponding one of outlet ports $165_A$ through $165_D$, via its drilled pathway in axle 161 and the sealed rotating groove under the corresponding one of axle spools $162_A$ through $162_D$. Preferred embodiments may advantageously hold and pass fluids or other materials in and through the immediately foregoing pathway structure at pressures up to 20 kpsi.

With reference now to FIGS. 22 and 25 and associated disclosure above, and with continuing reference to FIG. 26, it will be appreciated that outlet ports $165_A$ through $165_D$ may be connected to hose(s) 105 deployed within each string of KJL assemblies 103 deployed on MLR assembly $190_M$ via MLR axle hose connections, MLR spoke hoses and MLR rim hose connections (such connection structure hidden from view on FIGS. 22 and 25, but analogous to SLR axle hose connection $196_S$, SLR spoke hose $194_S$ and SLR rim hose connection $195_S$ illustrated and described above with respect to SLR assembly $190_S$ on FIG. 25). It will the therefore understood from the foregoing disclosure that each hose 105 deployed within each independently extendable and retractable string of KJL assemblies 103 deployed on MLR assembly $190_M$ may be addressed and supplied with fluid (or other materials) via a corresponding designated stationary inlet port $164_A$ through $164_D$ located on axle 161.

In exemplary embodiments, the drive structure on MLR assembly $190_M$ provides separate and independently operable drives, such as conventional chain and sprocket drives or belt and pulley drives, to rotate each MLR rim $191_M$ independently, in order to enable each corresponding string of KJL assemblies 103 to be extended or retracted independently, per user selection. It will be appreciated from the structure of MLR axle assembly $193_M$ as illustrated on FIG. 26 that direct drive structure (such as suggested above for SLR drive 198 in preferred embodiments of SLR assembly $190_S$ as illustrated on FIG. 25) is not optimal to provide independent drive structure to at least interior spools $162_B$ and $162_C$. Conventional belt or chain drives are more suitable to drive at least interior spools $162_B$ and $162_C$. Some embodiments of MLR $190_M$ may provide direct drive structure to drive end spools $162_A$ and $162_D$ on MLR axle assembly $193_M$, while other embodiment may provide other conventional drives, such as belt or chain drives, on end spools $162_A$ and $162_D$.

For the avoidance of doubt, it will be understood that throughout this disclosure, certain conventional structure has been omitted for clarity. For example, and without limitation, features of MLI assembly 100 are, in either "curved tube" or "straight tube" mode, advantageously supported by structural steel and other conventional support means, all of which has been omitted for clarity. Operation of MLI assembly 100 (including at adjustment assembly 120) is advantageously accomplished using conventional hydraulic, pneumatic or electrical apparatus, all of which has been also omitted for clarity.

Currently preferred embodiments of MLI assembly 100 may further be controlled to operate in user-selected options of manual, semi-automatic and automatic modes. A paradigm for optimal Scorpion System operating efficiency includes being able to program the MLI to run automatically. That is, to repeat a cycle of tubular interior processing operations (including cleaning and data acquisition operations) as a series of tubulars W are automatically and synchronously: (1) placed into position at the beginning of the cycle, (2) ejected at the end of the cycle, and then (3) replaced to start the next cycle. In automatic mode, the user may specify the sequence of operations of KJL assemblies 103 in a cycle on each tubular W. The cycle of lance operations will then be enabled and controlled automatically, including insertion and retraction of KJL assemblies 103 in sequence in and out of the tubular W, with corresponding repositioning of guide tubes 101 and stabbing guide 102 with respect to tubular W between each lance operation. The cycle may be repeated in automatic mode, as tubulars W are sequentially placed into position. In semi-automatic mode, the operation may be less than fully automatic in some way. For example, a cycle may be user-specified to only run once, so that tubulars W may be manually replaced between cycles. In manual mode, the user may dictate each lance operation individually, and the MLI may wait for further instruction after each lance operation.

The Scorpion System as described in this disclosure is designed to achieve the following operational goals and advantages:

Versatility.

The Scorpion System as disclosed herein has been described with respect to currently preferred embodiments. However, as has been noted repeatedly in this disclosure, such currently preferred embodiments are exemplary only, and many of the features, aspects and capabilities of the Scorpion System are customizable to user requirements. As a result the Scorpion System is operable on many diameters of tubular in numerous alternative configurations. Some embodiments may be deployed onto a U.S. Department of Transport standard semi-trailer for mobile service.

Substantially Lower Footprint of Cleaning Apparatus.

As noted above, conventionally, the cleaning of range 3 drill pipe requires a building at least 120 feet long. Certain configurations of the Scorpion System can, for example, clean range 3 pipe in a building of about half that length. Similar footprint savings are available for rig site deployments. As also noted above, a mobile embodiment of the Scorpion System is designed within U.S. Department of Transportation regulations to be mounted on an 18-wheel tractor-trailer unit and be transported on public roads in everyday fashion, without requirements for any special permits.

Dramatically Increased Production Rate in Cleaning.

An operational goal of the Scorpion System is to substantially reduce conventional cleaning time. Further, the integrated yet independently-controllable design of each phase of cleaning operations allows a very small operator staff (one person, if need be) to clean numerous tubulars consecutively in one session, with no other operator involvement needed unless parameters such as tubular size or cleaning requirements change. It will be further understood that in order to optimize productivity, consistency, safety and quality throughout all tubular operations, the systems enabling each phase or aspect of such operations are designed to run independently, and each in independently-selectable modes of automatic, semi-automatic or manual operation. When operator intervention is required, all adjustments to change, for example, modes of operation or tubular size being cleaned, such adjustments are advantageously enabled by hydraulically-powered actuators controlled by system software.

Improved Quality of Clean.

It is anticipated that the Scorpion System will open up the pores of the metal tubular much better than in conventional cleaning, allowing for a more thorough clean. In addition, the high rotational speed of the tubular during cleaning operations allows for a thorough clean without a spiral effect even though cleaning may optionally be done in one pass.

Although the present invention and its advantages have been described in detail, it should be understood that various changes, substitutions and alternations can be made herein without departing from the spirit and scope of the invention as defined by the appended claims.

We claim:

1. A method for performing operations on an internal surface of a hollow cylindrical tubular, the method comprising the steps of:
   (a) providing a hollow cylindrical tubular, the tubular having a cylindrical axis and an internal surface;
   (b) providing at least one rotatable reel;
   (c) spooling a lance on each reel, each lance comprising a plurality of generally straight hollow lance sections concatenated into an articulated string thereof, the string including lance sections having a generally trapezoidal profile deployed such that the string rolls up into a segmented curve when spooled on the reel;
   (d) connecting a tooling head to a distal end of each lance, each tooling head disposed to receive at least one of a plurality of interchangeable tools, the at least one tool selectably installed on the tooling head according to operations to be performed by the lance on the internal surface of the tubular;
   (e) deploying at least one hose inside each lance, each hose selected to suit each corresponding tool installed on the tooling head of each lance in step (d);
   (f) connecting each hose (1) at a distal end thereof to its corresponding tool, and (2) at a proximal end thereof to a supply selected to suit the tool connected to the distal end thereof;
   (g) positioning the at least one reel so that when the lance on each reel is unspooled and re-spooled, the tooling head travels along a locus substantially parallel with the cylindrical axis of the tubular;
   (h) deploying a stabbing mechanism between the at least one reel and the tubular, the stabbing mechanism disposed to position a selected one of the lances so that when the selected lance is unspooled off and re-spooled onto its corresponding reel, the tooling head on the selected lance travels along a locus inside the tubular and substantially parallel with cylindrical axis of the tubular, the stabbing mechanism further including at least one stabbing wheel, the at least one stabbing wheel disposed to contact the selected lance such that rotation of the at least one stabbing wheel in opposing directions causes the selected lance to unspool off and re-spool onto its corresponding reel;
   (i) rotating the tubular about its cylindrical axis;
   (j) rotating the at least one stabbing wheel so that, as the selected lance in step (h) unspools off and re-spools onto its corresponding reel, the tooling head on the selected lance travels into and out of the tubular; and
   (k) during step (j), delivering the supply in step (f) to tools on the tooling head on the selected lance.

2. The method of claim 1, in which the plurality of interchangeable tools in step (d) includes at least one tool selected from the group consisting of:
   (1) a high pressure liquid head;
   (2) a low pressure liquid head;
   (3) a rattling head cutter tool;
   (4) a brush;
   (5) a steam head;
   (6) a drift sleeve;
   (7) a pneumatic tool;
   (8) a compressed air head;
   (9) a gas head;
   (10) a data probe;
   (11) a video camera;
   (12) a still camera;
   (13) a thermal imaging device;
   (14) an acoustic sensor;
   (15) a magnetic resistivity sensor;
   (16) a hall effect sensor;
   (17) a data gathering sensor; and
   (18) an amplifier.

3. The method of claim 1, in which operations to be performed by the lance in step (d) include at least one operation selected from the group consisting of:
   (1) steam cleaning;
   (2) high pressure hydroblasting;
   (3) low pressure liquid spraying;
   (4) rattle head cutting;
   (5) abrasive cleaning;
   (6) brushing;
   (7) drift checking;
   (8) compressed air blowing;
   (9) gas drying;
   (10) streaming data acquisition;
   (11) static data acquisition;
   (12) visual inspection;
   (13) thermal imaging inspection;
   (14) magnetic flux inspection;
   (15) acoustic inspection;
   (16) magnetic resistivity inspection; and
   (17) sensor signal amplification.

4. The method of claim 1, in which the tubular is rotated in step (i) at operational speeds in a range of between about 0.01 rpm and about 1,750 rpm.

5. A method for performing operations on an internal surface of a hollow cylindrical tubular, the method comprising the steps of:
   (a) providing a hollow cylindrical tubular, the tubular having a cylindrical axis and an internal surface;
   (b) providing at least one lance, each lance disposed to be extendable and retractable, each lance comprising a plurality of generally straight hollow lance sections concatenated into an articulated string thereof, the string including lance sections having a generally trapezoidal profile deployed such that the string forms a segmented curve when the string is rolled back on itself;

(c) connecting a tooling head to a distal end of each lance, each tooling head disposed to receive at least one of a plurality of interchangeable tools, the at least one tool selectably installed on the tooling head according to operations to be performed by the lance on the internal surface of the tubular;

(d) deploying at least one hose inside each lance, each hose selected to suit each corresponding tool installed on the tooling head of each lance in step (c);

(e) connecting each hose (1) at a distal end thereof to its corresponding tool, and (2) at a proximal end thereof to a supply selected to suit the tool connected to the distal end thereof;

(f) providing a lance retainer, the lance retainer supporting each lance, the lance retainer further dispensing each lance during extension thereof, the lance retainer further storing each lance during retraction thereof;

(g) positioning the lance retainer so that the tooling head on each lance travels along a locus substantially parallel with the cylindrical axis of the tubular when the lance is extended and retracted;

(h) deploying a stabbing mechanism between the lance retainer and the tubular, the stabbing mechanism disposed to position a selected one of the lances so that when the selected lance is extended and retracted, the tooling head on the selected lance travels along a locus inside the tubular and substantially parallel with cylindrical axis of the tubular, the stabbing mechanism further including at least one stabbing wheel, the at least one stabbing wheel disposed to contact the selected lance such that rotation of the at least one stabbing wheel in opposing directions causes the selected lance to extend and retract;

(i) rotating the tubular about its cylindrical axis;

(j) rotating the at least one stabbing wheel so that, as the selected lance in step (h) extends and retracts, the tooling head on the selected lance travels into and out of the tubular; and (k) during step (j), delivering the supply in step (e) to tools on the tooling head on the selected lance.

6. The method of claim 5, in which the lance retainer is selected from the group consisting of:
(1) a multi-reel assembly on which a plurality of lances are spooled, one lance per reel;
(2) a single reel assembly on which a single lance is spooled;
(3) a multi-lance guide assembly inside which at least one lance is slideably received;
(4) an assembly of interconnected guide tubes, each guide tube slideably receiving one lance.

7. The method of claim 5, in which the lance retainer is a dual-mode retainer selected from the group consisting of (1) a multi-lance guide and (2) an assembly of interconnected guide tubes, and in which the dual-mode retainer is deployed in a retainer mode selected from the group consisting of (A) curved tube mode and (B) straight tube mode, wherein the dual-mode retainer is selectably interchangeable between curved tube mode and straight tube mode, wherein further a portion of the lance retainer is rolled back on itself in curved tube mode, and wherein further the lance retainer is substantially straight in straight tube mode.

8. The method of claim 6, in which all reels on the multi-reel assembly share a common axle.

9. The method of claim 5, in which the plurality of interchangeable tools in step (c) includes at least one tool selected from the group consisting of:
(1) a high pressure liquid head;
(2) a low pressure liquid head;
(3) a rattling head cutter tool;
(4) a brush;
(5) a steam head;
(6) a drift sleeve;
(7) a pneumatic tool;
(8) a compressed air head;
(9) a gas head;
(10) a data probe;
(11) a video camera;
(12) a still camera;
(13) a thermal imaging device;
(14) an acoustic sensor;
(15) a magnetic resistivity sensor;
(16) a hall effect sensor;
(17) a data gathering sensor; and
(18) an amplifier.

10. The method of claim 5, in which operations to be performed by the lance in step (c) include at least one operation selected from the group consisting of:
(1) steam cleaning;
(2) high pressure hydroblasting;
(3) low pressure liquid spraying;
(4) rattle head cutting;
(5) abrasive cleaning;
(6) brushing;
(7) drift checking;
(8) compressed air blowing;
(9) gas drying;
(10) streaming data acquisition;
(11) static data acquisition;
(12) visual inspection;
(13) thermal imaging inspection;
(14) magnetic flux inspection;
(15) acoustic inspection;
(16) magnetic resistivity inspection; and
(17) sensor signal amplification.

11. The method of claim 5, in which the tubular is rotated in step (i) at operational speeds in a range of between about 0.01 rpm and about 1,750 rpm.

12. A method for performing operations on an internal surface of a hollow cylindrical tubular, the method comprising the steps of:
(a) providing a hollow cylindrical tubular, the tubular having a cylindrical axis and an internal surface;
(b) providing at least one lance, each lance disposed to be extendable and retractable, each lance comprising a plurality of generally straight hollow lance sections concatenated into an articulated string thereof, the string including lance sections having a generally trapezoidal profile deployed such that the string forms a segmented curve when the string is rolled back on itself;
(c) connecting a tooling head to a distal end of each lance, each tooling head disposed to receive at least one tool, the at least one tool selectably installed on the tooling head according to operations to be performed by the lance on the internal surface of the tubular;
(d) deploying at least one hose inside each lance, each hose selected to suit each corresponding tool installed on the tooling head of each lance in step (c);

(e) connecting each hose (1) at a distal end thereof to its corresponding tool, and (2) at a proximal end thereof to a supply selected to suit the tool connected to the distal end thereof;

(f) providing a lance retainer, the lance retainer supporting each lance, the lance retainer further dispensing each lance during extension thereof, the lance retainer further storing each lance during retraction thereof;

(g) positioning the lance retainer so that the tooling head on each lance travels along a locus substantially parallel with the cylindrical axis of the tubular when the lance is extended and retracted;

(h) deploying a stabbing mechanism between the lance retainer and the tubular, the stabbing mechanism disposed to position a selected one of the lances so that when the selected lance is extended and retracted, the tooling head on the selected lance travels along a locus inside the tubular and substantially parallel with cylindrical axis of the tubular, the stabbing mechanism further including a reciprocating mechanism, the reciprocating mechanism disposed such that reciprocation thereof causes the selected lance to extend and retract;

(i) rotating the tubular about its cylindrical axis;

(j) causing the reciprocating mechanism to reciprocate so that, as the selected lance in step (h) extends and retracts, the tooling head on the selected lance travels into and out of the tubular; and (k) during step (j), delivering the supply in step (e) to tools on the tooling head on the selected lance.

13. The method of claim 12, in which at least one tool in step (c) is selected from the group consisting of:
(1) a high pressure liquid head;
(2) a low pressure liquid head;
(3) a rattling head cutter tool;
(4) a brush;
(5) a steam head;
(6), a drift sleeve;
(7) a pneumatic tool;
(8) a compressed air head;
(9) a gas head;
(10) a data probe;
(11) a video camera;
(12) a still camera;
(13) a thermal imaging device;
(14) an acoustic sensor;
(15) a magnetic resistivity sensor;
(16) a hall effect sensor;
(17) a data gathering sensor; and
(18) an amplifier.

14. The method of step 12, in which the reciprocating mechanism in step (h) comprises at least one stabbing wheel, the at least one stabbing wheel disposed to contact the selected lance such that rotation of the at least one stabbing wheel in opposing directions causes the selected lance to extend and retract.

15. The method of claim 12, in which the lance retainer is selected from the group consisting of:

(1) a multi-reel assembly on which a plurality of lances are spooled, one lance per reel;
(2) a single reel assembly on which a single lance is spooled;
(3) a multi-lance guide assembly inside which at least one lance is slideably received;
(4) an assembly of interconnected guide tubes, each guide tube slideably receiving one lance.

16. The method of claim 12, in which the lance retainer is a dual-mode retainer selected from the group consisting of (1) a multi-lance guide and (2) an assembly of interconnected guide tubes, and in which the dual-mode retainer is deployed in a retainer mode selected from the group consisting of (A) curved tube mode and (B) straight tube mode, wherein the dual-mode retainer is selectably interchangeable between curved tube mode and straight tube mode, wherein further a portion of the lance retainer is rolled back on itself in curved tube mode, and wherein further the lance retainer is substantially straight in straight tube mode.

17. The method of claim 15, in which all reels on the multi-reel assembly share a common axle.

18. The method of claim 12, in which the tooling head in step (c) is further disposed to provide at least one of a plurality of interchangeable tools, the plurality of interchangeable tools including at least one tool selected from the group consisting of:
(1) a high pressure liquid head;
(2) a low pressure liquid head;
(3) a rattling head cutter tool;
(4) a brush;
(5) a steam head;
(6) a drift checking tool;
(7) a probe; and
(8) a sensor.

19. The method of claim 12, in which operations to be performed by the lance in step (c) include at least one operation selected from the group consisting of:
(1) steam cleaning;
(2) high pressure hydroblasting;
(3) low pressure liquid spraying;
(4) rattle head cutting;
(5) abrasive cleaning;
(6) brushing;
(7) drift checking;
(8) compressed air blowing;
(9) gas drying;
(10) streaming data acquisition;
(11) static data acquisition;
(12) visual inspection;
(13) thermal imaging inspection;
(14) magnetic flux inspection;
(15) acoustic inspection;
(16) magnetic resistivity inspection; and
(17) sensor signal amplification.

20. The method of claim 12, in which the tubular is rotated in step (i) at operational speeds in a range of between about 0.01 rpm and about 1,750 rpm.

* * * * *